United States Patent
Lachenbruch et al.

(10) Patent No.: US 11,559,421 B2
(45) Date of Patent: Jan. 24, 2023

(54) PROTECTIVE DRESSING WITH REUSABLE PHASE-CHANGE MATERIAL COOLING INSERT

(71) Applicant: Hill-Rom Services, Inc., Batesville, IN (US)

(72) Inventors: Charles A Lachenbruch, Batesville, IN (US); Eric D Agdeppa, Cincinnati, OH (US); David L Ribble, Indianapolis, IN (US); Rachel L Williamson, Batesville, IN (US); Yongfeng Li, Singapore (SG); Chris Hill, Ravenshead (GB); Catherine A Vangilder, Blountville, TN (US); Jeffrey C Marrion, Acton, MA (US); David C Newkirk, Lawrenceburg, IN (US); Robert J Lawrence, Grand Rapids, MI (US); Craig M Meyerson, Syracuse, NY (US); Roger P Bonenfant, Victor, NY (US); John V Harmeyer, Cleves, OH (US); Steven D Baker, Beaverton, OR (US); Todd P O'Neal, Fairfield, OH (US); Ben Hertz, Acton, MA (US); Murray M Swoish, Caledonia, MI (US); Varad N Srivastava, Batesville, IN (US); David L Bedel, Oldenburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1010 days.

(21) Appl. No.: 15/189,459

(22) Filed: Jun. 22, 2016

(65) Prior Publication Data

US 2016/0374847 A1 Dec. 29, 2016

Related U.S. Application Data

(60) Provisional application No. 62/184,472, filed on Jun. 25, 2015.

(51) Int. Cl.
*A61F 13/00* (2006.01)
*A61F 5/30* (2006.01)
(Continued)

(52) U.S. Cl.
CPC ............... *A61F 5/30* (2013.01); *A61B 5/026* (2013.01); *A61B 5/4836* (2013.01);
(Continued)

(58) Field of Classification Search
None
See application file for complete search history.

(56) References Cited

U.S. PATENT DOCUMENTS

| 4,391,267 A | 7/1983 | Arrhenius |
| 4,504,402 A | 3/1985 | Chen et al. |

(Continued)

FOREIGN PATENT DOCUMENTS

| EP | 1635757 B1 | 6/2010 |
| EP | 2272473 A2 | 1/2011 |

(Continued)

OTHER PUBLICATIONS

US 6,645,236 B2, 11/2003, Lachenbruch et al. (withdrawn)
US 8,435,230 B2, 05/2013, Allison (withdrawn)
US 9,398,814 B2, 07/2016, Richards et al. (withdrawn)

*Primary Examiner* — Kim M Lewis
(74) *Attorney, Agent, or Firm* — Barnes & Thornburg LLP

(57) ABSTRACT

A protective dressing includes an outer dressing and an adhesive layer. The outer dressing includes an opening and a cavity sized to receive a phase-change material (PCM) insert inserted through the opening. The adhesive layer is configured to adhere to a patient's skin surrounding an anatomic site. When adhered to the patient's skin, the PCM insert modifies the patient's skin at the anatomic site. The
(Continued)

PCM insert may be removed and replaced with another PCM insert. For example, a warm PCM insert may be replaced with a refrigerated PCM insert. The opening of the outer dressing may be self-sealing. The opening of the outer dressing may be sealed with an upper layer dressing coupled to the PCM cooling insert.

15 Claims, 15 Drawing Sheets

(51) Int. Cl.
    *A61F 7/02*         (2006.01)
    *A61F 7/00*         (2006.01)
    *A61F 13/02*        (2006.01)
    *A61B 5/026*       (2006.01)
    *A61B 5/00*         (2006.01)
    *A61F 7/10*         (2006.01)
    *A61F 13/15*        (2006.01)

(52) U.S. Cl.
CPC .............. *A61F 7/0097* (2013.01); *A61F 7/02* (2013.01); *A61F 7/10* (2013.01); *A61F 13/00051* (2013.01); *A61F 13/00063* (2013.01); *A61F 13/00068* (2013.01); *A61F 13/023* (2013.01); *A61F 13/025* (2013.01); *A61F 13/0226* (2013.01); *A61B 2562/029* (2013.01); *A61B 2562/0247* (2013.01); *A61F 2007/0056* (2013.01); *A61F 2007/0219* (2013.01); *A61F 2007/0292* (2013.01); *A61F 2013/002* (2013.01); *A61F 2013/0057* (2013.01); *A61F 2013/00187* (2013.01); *A61F 2013/00553* (2013.01); *A61F 2013/00919* (2013.01); *A61F 2013/15024* (2013.01)

(56) References Cited

U.S. PATENT DOCUMENTS

| | | |
|---|---|---|
| 4,596,250 A | 6/1986 | Beisang et al. |
| 4,651,369 A | 3/1987 | Guldager |
| 4,667,658 A | 5/1987 | Guibert et al. |
| 4,671,267 A | 6/1987 | Stout et al. |
| 4,699,134 A | 10/1987 | Samuelsen et al. |
| 4,708,812 A | 11/1987 | Hatfield |
| 4,756,299 A | 7/1988 | Podella |
| 4,807,696 A | 2/1989 | Colvin et al. |
| 4,911,232 A | 3/1990 | Colvin et al. |
| 4,914,717 A | 4/1990 | Gibbon |
| 4,962,761 A | 10/1990 | Golden |
| 4,964,402 A | 10/1990 | Grim et al. |
| 4,981,135 A | 1/1991 | Hardy et al. |
| 4,999,867 A | 3/1991 | Toivio et al. |
| 5,010,608 A | 4/1991 | Barnett et al. |
| 5,033,136 A | 7/1991 | Elkins |
| 5,069,208 A | 12/1991 | Noppel et al. |
| 5,072,455 A | 12/1991 | St. Ours et al. |
| 5,088,487 A | 2/1992 | Turner |
| 5,094,238 A | 3/1992 | Gibbon |
| 5,181,905 A | 1/1993 | Flam |
| 5,190,031 A | 3/1993 | Guibert |
| 5,211,949 A | 5/1993 | Salyer |
| 5,275,156 A | 1/1994 | Milligan et al. |
| 5,277,180 A | 1/1994 | Angelillo et al. |
| 5,300,103 A | 4/1994 | Stempel |
| 5,366,801 A | 11/1994 | Bryant et al. |
| 5,431,622 A | 7/1995 | Pyrozyk et al. |
| 5,443,487 A | 8/1995 | Guibert et al. |
| 5,456,704 A | 10/1995 | Kilcullen |
| 5,456,852 A | 10/1995 | Isiguro |
| 5,486,207 A | 1/1996 | Mahawili |
| 5,511,260 A | 4/1996 | Dinsmoor, III et al. |
| 5,575,815 A | 11/1996 | Slepian et al. |
| 5,630,961 A | 5/1997 | Salee et al. |
| 5,637,389 A | 6/1997 | Colvin et al. |
| 5,691,040 A | 11/1997 | Barbeau et al. |
| 5,702,375 A | 12/1997 | Angelillo et al. |
| 5,713,143 A | 2/1998 | Kendall et al. |
| 5,722,482 A | 3/1998 | Buckley |
| 5,737,774 A | 4/1998 | Petty et al. |
| 5,750,962 A | 5/1998 | Hyatt et al. |
| 5,800,480 A | 9/1998 | Augustine et al. |
| 5,817,145 A | 10/1998 | Augustine et al. |
| 5,837,002 A | 11/1998 | Augustine et al. |
| 5,887,437 A | 3/1999 | Maxim |
| 5,926,884 A | 7/1999 | Biggie et al. |
| 5,932,129 A | 8/1999 | Hyatt et al. |
| 5,964,723 A | 10/1999 | Augustine |
| 5,984,953 A | 11/1999 | Sabin et al. |
| 5,993,480 A | 11/1999 | Burrows et al. |
| 6,004,662 A | 12/1999 | Buckley |
| 6,007,572 A | 12/1999 | Baldwin |
| 6,010,528 A | 1/2000 | Augustine et al. |
| 6,033,432 A | 3/2000 | Augustine et al. |
| 6,040,493 A | 3/2000 | Cooke et al. |
| 6,071,254 A | 6/2000 | Augustine |
| 6,071,304 A | 6/2000 | Augustine et al. |
| 6,080,189 A | 6/2000 | Augustine et al. |
| 6,083,254 A | 7/2000 | Evans |
| 6,083,256 A | 7/2000 | Der Ovanesian et al. |
| 6,095,992 A | 8/2000 | Augustine et al. |
| 6,102,936 A | 8/2000 | Augustine et al. |
| 6,113,561 A | 9/2000 | Augustine |
| 6,119,474 A | 9/2000 | Augustine et al. |
| 6,120,530 A | 9/2000 | Nuckols et al. |
| 6,123,716 A | 9/2000 | Augustine et al. |
| 6,132,455 A | 10/2000 | Shang |
| 6,179,879 B1 | 1/2001 | Robinson et al. |
| 6,183,855 B1 | 2/2001 | Buckley |
| 6,497,720 B1 | 12/2002 | Augustine et al. |
| 6,699,266 B2 | 3/2004 | Lachenbruch et al. |
| 6,755,852 B2 | 6/2004 | Lachenbruch et al. |
| 6,763,671 B1 | 7/2004 | Klett et al. |
| 6,772,825 B2 | 8/2004 | Lachenbruch et al. |
| 6,904,956 B2 | 6/2005 | Noel |
| 6,927,316 B1 * | 8/2005 | Fanes, Jr. ........... A41D 13/1245 |
| | | 602/14 |
| 6,996,864 B2 | 2/2006 | Call |
| 7,043,768 B2 | 5/2006 | Gogarty |
| 7,048,976 B2 | 5/2006 | Caceres et al. |
| 7,191,478 B2 | 3/2007 | Schmidt |
| 7,238,196 B2 | 7/2007 | Wibaux |
| 7,240,720 B2 | 7/2007 | Noel |
| 7,273,490 B2 | 9/2007 | Lachenbruch |
| 7,452,339 B2 | 11/2008 | Mattison |
| 7,588,548 B2 | 9/2009 | Kopreski |
| 7,708,338 B2 | 5/2010 | Wolas |
| 7,727,267 B2 | 6/2010 | Lachenbruch |
| 7,766,950 B2 | 8/2010 | Castellani et al. |
| 7,780,713 B2 | 8/2010 | Roberts |
| 7,793,372 B2 | 9/2010 | Lean et al. |
| 7,854,754 B2 | 12/2010 | Ting et al. |
| 8,002,721 B2 | 8/2011 | Bretl et al. |
| 8,062,343 B2 | 11/2011 | Augustine et al. |
| 8,065,763 B2 | 11/2011 | Brykalski et al. |
| 8,100,848 B2 | 1/2012 | Wilkes et al. |
| 8,129,580 B2 | 3/2012 | Wilkes et al. |
| 8,133,211 B2 | 3/2012 | Cavanaugh, II et al. |
| 8,147,468 B2 | 4/2012 | Barta et al. |
| 8,167,856 B2 | 5/2012 | Kazala, Jr. et al. |
| 8,172,816 B2 | 5/2012 | Kazala, Jr. et al. |
| 8,181,290 B2 | 5/2012 | Brykalski et al. |
| 8,187,237 B2 | 5/2012 | Seegert |
| 8,188,331 B2 | 5/2012 | Barta et al. |
| 8,191,187 B2 | 6/2012 | Brykalski et al. |
| 8,192,474 B2 | 6/2012 | Levinson |
| 8,202,261 B2 | 6/2012 | Kazala, Jr. et al. |
| 8,241,261 B2 | 8/2012 | Randolph et al. |
| 8,275,442 B2 | 9/2012 | Allison |
| 8,277,497 B2 | 10/2012 | Noel |
| 8,285,390 B2 | 10/2012 | Levinson et al. |
| 8,292,936 B2 | 10/2012 | Jung |

(56) References Cited

U.S. PATENT DOCUMENTS

| | | | |
|---|---|---|---|
| 8,292,937 B2 | 10/2012 | von Hoffmann et al. | |
| 8,303,857 B2 | 11/2012 | Seeboth et al. | |
| 8,326,426 B2 | 12/2012 | Thornton et al. | |
| 8,327,477 B2 | 12/2012 | Lachenbruch et al. | |
| 8,332,975 B2 | 12/2012 | Brykalski et al. | |
| 8,337,539 B2 | 12/2012 | Ting et al. | |
| 8,376,232 B2 | 2/2013 | Eckstein et al. | |
| 8,397,518 B1 * | 3/2013 | Vistakula | A61F 7/02 62/3.5 |
| 8,399,730 B2 | 3/2013 | Kazala, Jr. et al. | |
| 8,402,579 B2 | 3/2013 | Marquette et al. | |
| 8,418,286 B2 | 4/2013 | Brykalski et al. | |
| 8,523,927 B2 | 9/2013 | Levinson et al. | |
| 8,528,833 B2 | 9/2013 | Munson | |
| 8,578,527 B2 | 11/2013 | Lachenbruch et al. | |
| 8,603,073 B2 | 12/2013 | Allison | |
| 8,617,230 B2 | 12/2013 | Diller et al. | |
| 8,621,687 B2 | 1/2014 | Brykalski et al. | |
| 8,641,745 B2 | 2/2014 | Warner et al. | |
| 8,673,448 B2 | 3/2014 | Hartmann et al. | |
| 8,702,774 B2 | 4/2014 | Baker et al. | |
| 8,722,959 B2 | 5/2014 | Wilkes et al. | |
| 8,732,874 B2 | 5/2014 | Brykalski et al. | |
| 8,782,830 B2 | 7/2014 | Brykalski et al. | |
| 8,800,078 B2 | 8/2014 | Lachenbruch et al. | |
| 8,856,993 B2 | 10/2014 | Richards et al. | |
| 8,858,971 B2 | 10/2014 | Rao | |
| 8,887,619 B2 | 11/2014 | Kallmyer et al. | |
| 8,893,329 B2 | 11/2014 | Petrovski et al. | |
| 8,933,140 B2 | 1/2015 | Peterson et al. | |
| 8,937,212 B2 | 1/2015 | Fogg et al. | |
| 9,009,892 B2 | 4/2015 | Lachenbruch et al. | |
| 9,084,764 B2 | 7/2015 | Rao | |
| 9,089,462 B1 | 7/2015 | Lafleche | |
| 9,125,497 B2 | 9/2015 | Brykalski et al. | |
| 9,132,031 B2 | 9/2015 | Levinson et al. | |
| 9,158,141 B2 | 10/2015 | DeFranks | |
| 9,234,059 B2 | 1/2016 | Hartmann et al. | |
| 9,265,654 B2 | 2/2016 | Gallaher | |
| 9,333,136 B2 | 5/2016 | Gibson et al. | |
| 9,339,412 B2 | 5/2016 | Diller et al. | |
| 9,375,345 B2 | 6/2016 | Levinson et al. | |
| 9,408,475 B2 | 8/2016 | Mikkelsen et al. | |
| 2001/0039391 A1 | 11/2001 | Augustine | |
| 2003/0046762 A1 | 3/2003 | Stolpmann | |
| 2003/0109816 A1 | 6/2003 | Lachenbruch et al. | |
| 2003/0109908 A1 | 6/2003 | Lachenbruch et al. | |
| 2003/0109910 A1 | 6/2003 | Lachenbruch et al. | |
| 2005/0049662 A1 | 3/2005 | Purcell | |
| 2005/0076715 A1 | 4/2005 | Kuklis et al. | |
| 2005/0145372 A1 | 7/2005 | Noel | |
| 2006/0100682 A1 | 5/2006 | Koffroth | |
| 2006/0260058 A1 | 11/2006 | Schmidt | |
| 2006/0276089 A1 | 12/2006 | Amarasinghe et al. | |
| 2007/0098973 A1 | 5/2007 | Wagner et al. | |
| 2007/0101478 A1 | 5/2007 | Koscheyev et al. | |
| 2007/0135878 A1 | 6/2007 | Lachenbruch et al. | |
| 2007/0173154 A1 | 7/2007 | Hartmann et al. | |
| 2007/0193278 A1 | 8/2007 | Polacek et al. | |
| 2007/0198071 A1 | 8/2007 | Ting et al. | |
| 2007/0250025 A1 | 10/2007 | Sams et al. | |
| 2007/0255362 A1 | 11/2007 | Levinson et al. | |
| 2008/0015665 A1 | 1/2008 | Lachenbruch | |
| 2008/0028517 A1 | 2/2008 | Schmidt | |
| 2008/0077201 A1 | 3/2008 | Levinson et al. | |
| 2008/0120761 A1 | 5/2008 | Yang et al. | |
| 2008/0140166 A1 | 6/2008 | von Hoffman et al. | |
| 2008/0234789 A1 | 9/2008 | Freeland et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |
| 2009/0076574 A1 | 3/2009 | Noel | |
| 2009/0076575 A1 | 3/2009 | Noel | |
| 2009/0293887 A1 | 12/2009 | Wilkes et al. | |
| 2009/0299249 A1 | 12/2009 | Wilkes et al. | |
| 2009/0299256 A1 | 12/2009 | Barta et al. | |
| 2009/0299307 A1 | 12/2009 | Barta et al. | |
| 2009/0299308 A1 | 12/2009 | Kazala, Jr. et al. | |
| 2009/0299442 A1 | 12/2009 | Vergona et al. | |
| 2010/0011489 A1 | 1/2010 | Goldmann et al. | |
| 2010/0012883 A1 | 1/2010 | Hartmann et al. | |
| 2010/0015430 A1 | 1/2010 | Hartmann et al. | |
| 2010/0016513 A1 | 1/2010 | Hartmann et al. | |
| 2010/0089381 A1 | 4/2010 | Bolmer et al. | |
| 2010/0227542 A1 | 9/2010 | Goldmann et al. | |
| 2010/0263128 A1 | 10/2010 | Lean et al. | |
| 2010/0274331 A1 | 10/2010 | Williamson et al. | |
| 2010/0280582 A1 | 11/2010 | Baker et al. | |
| 2011/0024076 A1 | 2/2011 | Lachenbruch et al. | |
| 2011/0041780 A1 | 2/2011 | Hurwitz | |
| 2011/0092890 A1 | 4/2011 | Stryker et al. | |
| 2011/0127248 A1 | 6/2011 | Moreshead | |
| 2011/0128686 A1 | 6/2011 | Moreshead | |
| 2011/0128726 A1 | 6/2011 | Moreshead | |
| 2011/0130813 A1 | 6/2011 | Moreshead | |
| 2011/0183712 A1 | 7/2011 | Eckstein et al. | |
| 2012/0023664 A1 | 2/2012 | Joo et al. | |
| 2012/0095538 A1 | 4/2012 | Dow | |
| 2012/0180225 A1 | 7/2012 | Gladney et al. | |
| 2012/0330213 A1 | 12/2012 | Valdez | |
| 2013/0043232 A1 | 2/2013 | Whitworth et al. | |
| 2013/0205462 A1 | 8/2013 | Kitaura et al. | |
| 2013/0296769 A1 | 11/2013 | Howell et al. | |
| 2014/0005759 A1 * | 1/2014 | Fahey | A61F 7/10 607/99 |
| 2014/0141233 A1 | 5/2014 | Crawford et al. | |
| 2014/0221962 A1 | 8/2014 | Ribble et al. | |
| 2014/0266643 A1 | 9/2014 | Receveur et al. | |
| 2014/0304915 A1 | 10/2014 | Lachenbruch | |
| 2014/0359939 A1 | 12/2014 | Carlitz | |
| 2015/0013073 A1 | 1/2015 | Schwirian et al. | |
| 2015/0101788 A1 * | 4/2015 | Smith | A61F 7/007 62/3.5 |
| 2015/0290042 A1 * | 10/2015 | Freer | A61F 13/022 602/43 |
| 2016/0015280 A1 * | 1/2016 | Hyde | G16H 50/30 600/301 |
| 2016/0178251 A1 * | 6/2016 | Johnson | A61F 7/007 62/3.5 |
| 2016/0235210 A1 | 8/2016 | Lachenbruch et al. | |
| 2017/0128258 A1 * | 5/2017 | Diller | A61F 7/007 |

FOREIGN PATENT DOCUMENTS

| | | | | |
|---|---|---|---|---|
| EP | 2344988 A1 | 7/2011 | | |
| EP | 1895874 B1 | 5/2012 | | |
| EP | 2276437 B1 | 12/2012 | | |
| EP | 2594234 A2 | 5/2013 | | |
| EP | 2344988 B1 | 8/2013 | | |
| EP | 2702966 A2 | 3/2014 | | |
| FR | 2643814 A1 | 9/1990 | | |
| FR | 2867672 A1 | 9/2005 | | |
| GB | 2445760 A * | 7/2008 | ....... | A61F 13/00038 |
| GB | 2510154 A | 7/2014 | | |
| GB | 2514594 A | 12/2014 | | |
| WO | 2005006896 A1 | 1/2005 | | |
| WO | 2005016074 A1 | 2/2005 | | |
| WO | 2005067837 A1 | 7/2005 | | |
| WO | 2006001982 A2 | 1/2006 | | |
| WO | 2006122555 A1 | 11/2006 | | |
| WO | 2006122556 A1 | 11/2006 | | |
| WO | 2007133839 A1 | 11/2007 | | |
| WO | 2009046155 A1 | 4/2009 | | |
| WO | 2010075293 A1 | 7/2010 | | |
| WO | 2012174276 A2 | 12/2012 | | |
| WO | 2013177148 A1 | 11/2013 | | |
| WO | 2014008182 A1 | 1/2014 | | |
| WO | 2014035792 A1 | 3/2014 | | |
| WO | 2014182767 A1 | 11/2014 | | |
| WO | 2015006407 A1 | 1/2015 | | |
| WO | 2015137999 A1 | 9/2015 | | |

(56) References Cited

FOREIGN PATENT DOCUMENTS

* cited by examiner

PROTECTIVE DRESSING WITH REUSABLE PHASE-CHANGE MATERIAL COOLING INSERT

CROSS REFERENCE TO RELATED APPLICATIONS

The present application claims the benefit, under 35 U.S.C. § 119(e), of U.S. Provisional Application No. 62/184,472, filed Jun. 25, 2015, which is hereby incorporated by reference herein.

BACKGROUND

The present disclosure is related to protective dressings or bandages used to prevent ischemic pressure ulcers. More specifically, the present disclosure is related to a dressing which receives a reusable cooling insert containing a phase-change material.

Pressure ulcers and deep tissue injury may be caused by excessive pressure on a patient's skin over time, for example when a patient uses a hospital bed or other patient support apparatus for an extended period. Protective barrier dressings (e.g., bandages) or surfaces (e.g., mattresses) may be used to prevent pressure ulcers by reducing friction, surface shear, and/or moisture on the patient's skin. Cooling of the patient's skin may also have a significant impact on prevention and treatment of pressure ulcers and tissue damage. In particular, reduced temperature may reduce moisture accumulation on the skin. Also, reduced temperature may reduce tissue metabolic rate, which may also reduce the severity and depth of tissue damage. As a result, cooling the patient's skin may allow the skin to tolerate a given pressure for a longer time period. Traditional protective barrier dressings may not reduce skin temperature and, indeed, may tend to increase skin temperature. Micro-climate management (MCM) layers capable of reducing the temperature of patient support surfaces (e.g. mattresses) are known, but may be incompatible with some care settings and/or susceptible to interference from patient linens.

A phase change material (PCM) is a substance with a high heat of fusion or v that is capable of storing and releasing large amounts of heat energy when melting or freezing. In particular, when a PCM in the solid phase reaches the temperature at which it changes phase (the melting temperature), the PCM may absorb large amounts of heat at an almost constant temperature. PCMs are used in many industries, including building and construction, textiles, refrigeration, and others. PCMs may be used in textiles for thermal comfort in a consumer application.

SUMMARY

The present application discloses one or more of the features recited in the appended claims and/or the following features which, alone or in any combination, may comprise patentable subject matter:

According to an aspect of the present disclosure, an apparatus for modifying the temperature of a person's skin in a localized region comprises, a skin contacting surface, a heat sink, and a flow path to allow heat to flow between the skin and the heat sink. The heat sink has a first temperature different from the temperature of the skin being contacted by the skin contacting surface to create a temperature gradient between the skin and the heat sink.

In some embodiments, the apparatus comprises a protective dressing including a lower adhesive layer and an upper adhesive layer. The lower adhesive layer has (i) an adhesive lower surface capable of adhering to a person's skin surrounding an anatomic site and (ii) an upper surface having an opening. The upper adhesive layer is configured to be removably coupled to the upper surface of the lower adhesive layer. The heat sink is coupled to the upper adhesive layer and is configured to be positioned within the opening of the upper surface of the lower adhesive layer and to vary temperature of the skin at the anatomic site when the upper adhesive layer is removably coupled to the upper surface of the lower adhesive layer.

In some embodiments, the apparatus comprises a protective dressing including a cushion layer adapted to be in contact with the skin at an anatomic site and an outer adhesive layer. The heat sink may be coupled to the cushion layer. The outer adhesive layer is coupled to the insert and the cushion layer and is capable of adhering to the person's skin surrounding an anatomic site.

In some embodiments, the apparatus comprises a conductive pad configured to underlie a person's body region subject to pressure ulcers and adapted to be in contact with the person's skin. The flow path may include at least one conductive conduit laterally extending from the conductive pad, the conductive conduit having a free end. The heat sink may be coupled to the free end to transfer heat between the heat sink and the conductive pad through the conductive conduit.

In some embodiments, the free end includes at least one compartment having an opening and a cavity, the cavity sized to receive a replaceable heat sink through the opening.

In some embodiments, the apparatus includes a thermally conductive pad configured to include the skin contacting surface. The heat sink may comprise a thermally conductive patch configured to be mounted on a patient support apparatus. The flow path may facilitate the flow of heat between the thermally conductive pad and the heat sink.

In some embodiments, the apparatus comprises a thermoelectric device that includes a first surface that is the skin contacting surface and a second surface, positioned away from the skin contacting surface. The apparatus may further comprise an adhesive layer configured to overlie the thermoelectric device to secure the thermoelectric device to the skin. The apparatus may still further comprise a power source operable to cause the thermoelectric device to transfer heat between the first surface of the thermoelectric device and the second surface of the thermoelectric device. The flow path may facilitate the transfer of heat between the heat sink and the second surface of thermoelectric device.

In some embodiments, the apparatus further comprises a temperature sensor for determining the temperature of the surface of the skin.

In some embodiments, the apparatus further comprises a pressure sensor for determining the pressure applied to the surface of the skin.

In some embodiments, the apparatus further comprises a moisture sensor for determining the moisture at the surface of the skin. In some embodiments, the apparatus further comprises a perfusion sensor for determining the perfusion at the anatomical site. The perfusion sensor may determine perfusion at the surface or deeper in the tissue.

In some embodiments, the power source may be configured to vary the operation of the thermoelectric device in response to a condition at the surface of the skin detected by one or more sensors.

In some embodiments, the power source wirelessly transfers power to the thermoelectric device.

In some embodiments, the heat sink comprises a phase-change material.

In some embodiments, the heat sink comprises a foam carrier that comprises a phase-change material.

In some embodiments, the heat sink has an initial temperature that is lower than the skin temperature such that heat flows away from the skin.

In some embodiments, the heat sink has an initial temperature that is higher than the skin temperature such that heat flows to the skin.

According to another aspect of the present disclosure, a protective dressing comprises an outer dressing, a skin-contacting surface coupled to the outer dressing, and an adhesive layer coupled to the outer dressing. The outer dressing has an opening and an interior cavity sized to receive a reusable or disposable phase-change material cooling insert inserted through the opening. The skin-contacting surface is adapted to be in contact with a person's skin at an anatomic site, and configured to be cooled by the phase-change material cooling insert when the phase-change material cooling insert is inserted in the outer dressing. The adhesive layer is capable of adhering to the person's skin surrounding the anatomic site.

In some embodiments, the protective dressing further includes a reusable phase-change material cooling insert positioned in the interior cavity of the outer dressing. The phase-change material cooling insert includes a phase-change material. In some embodiments, the reusable phase-change material cooling insert further comprises a gel carrier that includes the phase-change material. In some embodiments, the reusable phase-change material cooling insert further comprises an elastomeric carrier that includes the phase-change material. In some embodiments, the reusable phase-change material cooling insert further comprises an oil carrier that includes the phase-change material. In some embodiments, the phase-change material is a hexane. In some embodiments, the phase-change material is an anhydrous salt. In some embodiments, the cross-section of the cooling insert and/or the pad may be designed to minimize the pressure on an anatomic location, for example, the cooling insert may be thinner in the area that directly overlays a bony prominence such as the trocanter, scapula, heel, sacrum, or the like, than it is in the area surrounding the bony prominence In some embodiments, the opening is a self-sealing opening.

According to another aspect of the present disclosure, a protective dressing system comprises a lower adhesive layer, an upper adhesive layer, and a phase-change material cooling insert coupled to the upper adhesive layer. The lower adhesive layer has an adhesive lower surface capable of adhering to a person's skin surrounding an anatomic site and an upper surface having an opening. The upper adhesive layer is configured to be removably coupled to the upper surface of the lower adhesive layer. The phase-change material cooling insert comprises a phase-change material, and the phase-change material cooling insert is configured to be positioned within the opening of the upper surface of the lower adhesive layer and to cool the person's skin at the anatomic site when the upper adhesive layer is removably coupled to the upper surface of the lower adhesive layer.

In some embodiments, the phase-change material cooling insert comprises a skin-contacting surface adapted to contact the person's skin at the anatomic site. In some embodiments, the phase-change material cooling insert further comprises a foam carrier that includes the phase change material. In some embodiments, the foam carrier comprises an elastomeric foam carrier.

In some embodiments, the protective dressing system further includes a foam protective layer coupled to the lower adhesive layer. The foam protective layer includes a skin-contacting surface adapted to contact the person's skin at the anatomic site. The phase-change material cooling insert is configured to be positioned above the foam protective layer when the upper adhesive layer is removably coupled to the upper surface of the lower adhesive layer. In some embodiments, the phase-change material cooling insert further comprises a gel carrier that includes the phase-change material. In some embodiments, the phase-change material cooling insert further comprises an elastomeric carrier that includes the phase-change material. In some embodiments the phase-change material cooling insert further comprises an oil carrier that includes the phase-change material.

According to yet another aspect of the present disclosure, a method for applying a protective dressing to a person comprises selecting a stability temperature for an anatomic site of the person, selecting a refrigerated phase change material cooling insert as a function of the selected stability temperature, inserting the refrigerated phase change material cooling insert into an opening of a protective dressing, and adhering an adhesive layer of the protective dressing to the person. The phase change material cooling insert cools the anatomic site of the person in response inserting the refrigerated phase change material cooling insert into the opening of the protective dressing and adhering the adhesive layer of the protective dressing to the person.

In some embodiments, the method further comprises sealing the opening of the protective dressing in response to inserting the selected phase change material cooling insert into the opening. The opening comprises a self-sealing opening.

In some embodiments, the method further comprises adhering an upper adhesive layer coupled to the phase change material cooling insert to the protective dressing to seal the opening of the protective dressing in response to inserting the selected phase change material cooling insert into the opening.

In some embodiments, the method further comprises removing the phase change material cooling insert from the protective dressing through the opening of the protective dressing, selecting a second refrigerated phase change material cooling insert as a function of the selected stability temperature, and inserting the second refrigerated phase change material cooling insert into the opening of the protective dressing in response to removing the phase change material cooling insert from the protective dressing.

According to another aspect of the present disclosure, a protective dressing comprises a cushion layer adapted to be in contact with a person's skin at an anatomic site, an insert coupled to the cushion layer, the insert having a phase change material, and an outer adhesive layer coupled to the insert and the cushion layer. The outer adhesive layer is capable of adhering to the person's skin surrounding an anatomic site. The person's skin at the anatomic site is configured to be cooled by a vaporization of the phase-change material.

In some embodiments, the insert further comprises a gel carrier that includes the phase-change material. In some embodiments, the insert further comprises an elastomeric carrier that includes the phase-change material. In some embodiments, the insert further comprises an oil carrier that includes the phase-change material. In some embodiments, the phase-change material comprises a hexane. In some embodiments, the phase-change material comprises an anhydrous salt.

According to another aspect of the present disclosure, a thermally conductive apparatus for removal of heat of a person supported on a patient support surface comprises a conductive pad configured to underlie a person's body region subject to pressure ulcers and adapted to be in contact with a person's skin, at least one conductive conduit laterally extending from the conductive pad, and a heat sink coupled to the free end to withdraw heat from the conductive pad via the conductive conduit. The conductive conduit includes a free end.

In some embodiments, the free end further comprises at least one compartment having an opening and a cavity, wherein the cavity is sized to receive a replaceable heat sink inserted through the opening.

In some embodiments, the heat sink is the phase-change material cooling insert adapted to contact the person's skin at the anatomic site.

In some embodiments, the phase-change material cooling insert further comprises a gel carrier that includes the phase-change material. In some embodiments, the phase-change material cooling insert further comprises an elastomeric carrier that includes the phase-change material. In some embodiments, the phase-change material cooling insert further comprises an oil carrier that includes the phase-change material. In some embodiments, the phase-change material comprises a hexane. In some embodiments, the phase-change material comprises an anhydrous salt.

In some embodiments, the compartment is configured to rest below a patient support when the conductive pad is positioned underneath a person supported on the patient support surface.

In some embodiments, the free end is coupled to a metal frame of a patient support surface.

According to another aspect of the present disclosure, a conductive system for removal of heat of a patient supported on a patient support surface comprises a thermally conductive pad having a plurality of conductive regions and an adhesive layer and a conductive patch mounted on the patient support surface, configured to underlie the thermally conductive pad. The thermally conductive pad is adapted to underlie a patient's anatomic site subject to pressure ulcers and be in contact with a patient's skin at the anatomic site. The thermally conductive pad is configured to withdraw heat from the patient's anatomic site when the thermally conductive pad is in contact with the conductive patch.

In some embodiments, the conductive patch is a heat sink configured to withdraw heat from the thermally conductive pad.

According to another aspect of the present disclosure, a wearable conductive strap comprises a highly conductive material and an insulated lining configured to encase the conductive material. The insulated lining includes a first opening and a second opening. The first opening is configured to underlie an anatomic site of a patient, and the second opening is configured to be positioned on the ventral side of the patient, wherein heat from the first opening is transferred to the second opening via the conductive material and is released at the second opening. The wearable conductive strap is configured to extend around an anatomic site of a patient.

In some embodiments, the anatomic site is a torso area of the patient.

In some embodiments, the conductive material comprises a metal such as copper, silver, gold, or metal alloy such as brass or bronze. In some embodiments, the conductive material comprises carbon fibers. In some embodiments, the conductive material comprises graphene.

In some embodiments, the insulated lining comprises an inner insulated lining and an outer insulated lining, the inner insulated lining includes a first opening, and the outer insulated lining includes a second opening.

In some embodiments, the first opening is configured to be in contact with the anatomic site. In some embodiments, the second opening is configured to expose the conductive material to ambient air. In some embodiments, the first opening is configured to conductively withdraw heat from the anatomic site to the second opening. In some embodiments, the second opening is exposed to ambient air and is configured to convectively provide preventative cooling to the anatomic site of a patient.

According to another aspect of the present disclosure, a thermoelectric system comprises a thermoelectric pad, a heat sink, and a power source. The thermoelectric pad further comprises an outer adhesive layer, a skin-contacting layer, and a thermoelectric material positioned between the outer adhesive layer and the skin-contacting layer. The skin-contacting layer is adapted to be in contact with a patient's skin at an anatomic site. The thermoelectric pad operable in either the prevention mode or a therapy mode. The prevention mode corresponds to a first temperature and a treatment mode corresponds to a second temperature to target a predetermined temperature of the patient's skin at an anatomic site.

In some embodiments, the thermoelectric pad further includes an integrated temperature sensor. In some embodiments, the thermoelectric pad further includes an integrated pressure sensor. In some embodiments, the thermoelectric pad further includes an integrated moisture sensor. In some embodiments, the mode of the thermoelectric pad is selected by changing a polarity of the thermoelectric material. In some embodiments the thermoelectric pad further includes an integrated sensor that provides a measure proportional to heat flux. For example, a sensor that measures the thermal difference at two points separated along the direction of the temperature gradient. The system may use feedback control to modulate the cooling as a function of a measured input such as blood flow, vasoconstriction, skin temperature or other physiological parameter. Blood flow and vasoconstriction can be measured for example using different wavelengths of light ranging from at least green to the near infrared and from ultrasound. Temperature can be measured using an infrared detector, thermocouple, thermistor, thermopile and the like.

In some embodiments, the prevention mode is design to provide a focal cooling at the patient's anatomic site. In some embodiments, the treatment mode is design to provide a focal heating at the patient's anatomic site. In some embodiments, the system alternates heating and cooling of the patient's anatomical site.

In some embodiments, the power source is configured to wirelessly transfer a supply of power from the power source to a thermoelectric pad. In some embodiments, the power source is mounted in the patient support apparatus. In some embodiments, the power source is directly coupled to the thermoelectric pad. In some embodiments, the thermoelectric system further comprises a heat sink.

According to another aspect of the present disclosure, a ticking layer of a patient support surface comprises a plurality of conductive strips and a heat sink coupled to the plurality of conductive strips.

In some embodiments, the plurality of conductive strips is configured to underlie a patient body region subject to pressure ulcers.

In some embodiments, the plurality of conductive strips is configured to be positioned at a foot area of the patient support surface.

In some embodiments, the plurality of conductive strips further includes an adhesive layer, such that the plurality of conductive strips is removable and repositionable on the ticking layer of the patient support surface.

According to another aspect of the present disclosure, a conductive mat comprises a conductive fibers and a compartment. The conductive fibers are configured to underlie a patient's anatomic site, and the compartment includes an opening and a cavity extended thereof, such that the conductive fibers extend along the cavity. The cavity is sized to receive a heat sink inserted through the opening. The cavity opening may allow replacement of the heat sink without moving or otherwise disturbing the patient.

In some embodiments, the heat sink is a reusable phase-change material cooling insert.

In some embodiments, the conductive material comprises carbon fibers. In some embodiments, the conductive fibers are arranged in a mesh configuration. In some embodiments, the conductive fibers are arranged in spiral configuration.

In some embodiments, portions of the conductive mat that are not covered by the patient are cooled convectively using ambient air. In other embodiments forced convection may be used.

In some embodiments, the conductive mat is reusable.

According to another aspect of the present disclosure, a conductive garment comprises at least one conductive region having a conductive material. The conductive material is configured to be positioned around a torso region of a patient.

In some embodiments, portions of the conductive garment that are not covered by the patient are cooled convectively using ambient air.

According to another aspect of the present disclosure, a focal cooling device comprises a protective upper layer, a middle layer, a lower adhesive layer, and a phase-change material cooling insert. The lower adhesive layer is adapted to be in contact with a patient's skin at an anatomic site. The phase-change material cooling insert is positioned between the protective upper layer and the middle layer. The phase-change material cooling insert includes a phase-change material and conductive material to remove the heat from the patient's anatomic site.

In some embodiments, the conductive material comprises pitch-based carbon fibers.

In some embodiments, the conductive material vertically extends along outer edges of the phase-change material cooling insert.

In some embodiments, the conductive material extends radially such that the phase-change material cooling insert peripherally removes the heat from the patient's skin to provide cooling capacity to a central region of the dressing.

In some embodiments, the protective upper layer includes an opening and an interior cavity, wherein the cavity is sized to receive a phase-change material through the opening.

BRIEF DESCRIPTION OF THE DRAWINGS

The detailed description particularly refers to the accompanying figures in which.

DETAILED DESCRIPTION OF THE DRAWINGS

A protective dressing 10 illustratively includes a barrier dressing 12 and an adhesive layer 14 as shown in FIGS. 1-4. The protective dressing 10 may be adhered to a patient's skin at a vulnerable site, such as the patient's sacral area, to prevent potential pressure ulcers or other tissue damage. The barrier dressing 12 is a medical dressing or bandage impermeable to moisture or air. In some embodiments, the barrier dressing 12 may be air and/or moisture permeable as will be discussed in further detail below. The barrier dressing 12 is constructed of soft, compliant material with layers that slide readily over one another so that the protective dressing 10 imposes limited pressure and shear to the vulnerable site. For example, the barrier dressing 12 includes one or more foam layers or other compliant material. The adhesive layer 14 is embodied as an adhesive capable of adhering the protective dressing 10 to the patient's skin. In some embodiments, the protective dressing 10 may remain on the patient's skin for the duration of hospitalization for acute care (e.g., four to five days).

Figure 1:
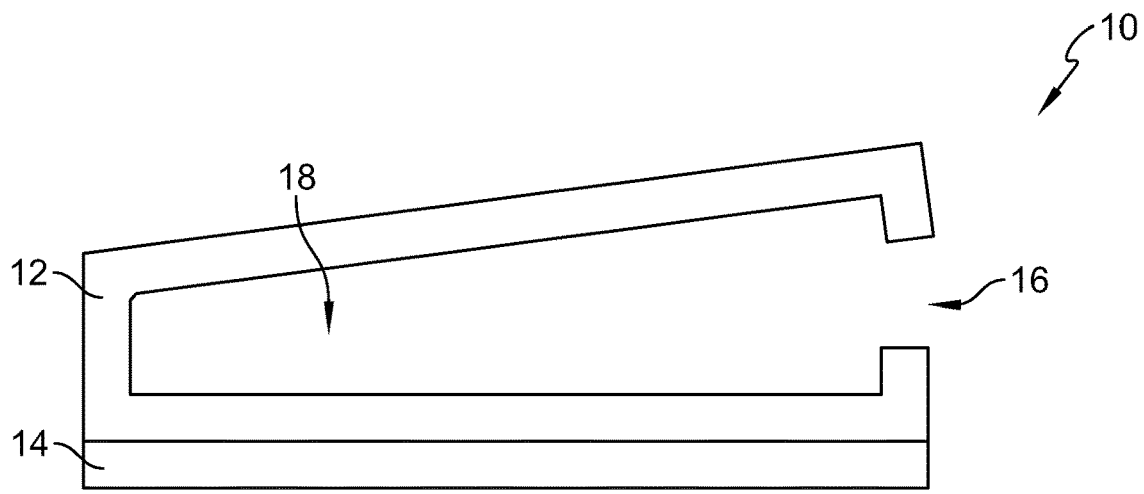
FIG. 1 is a cross-sectional side view of a first protective dressing with an opening in an open position.
Figure 2:
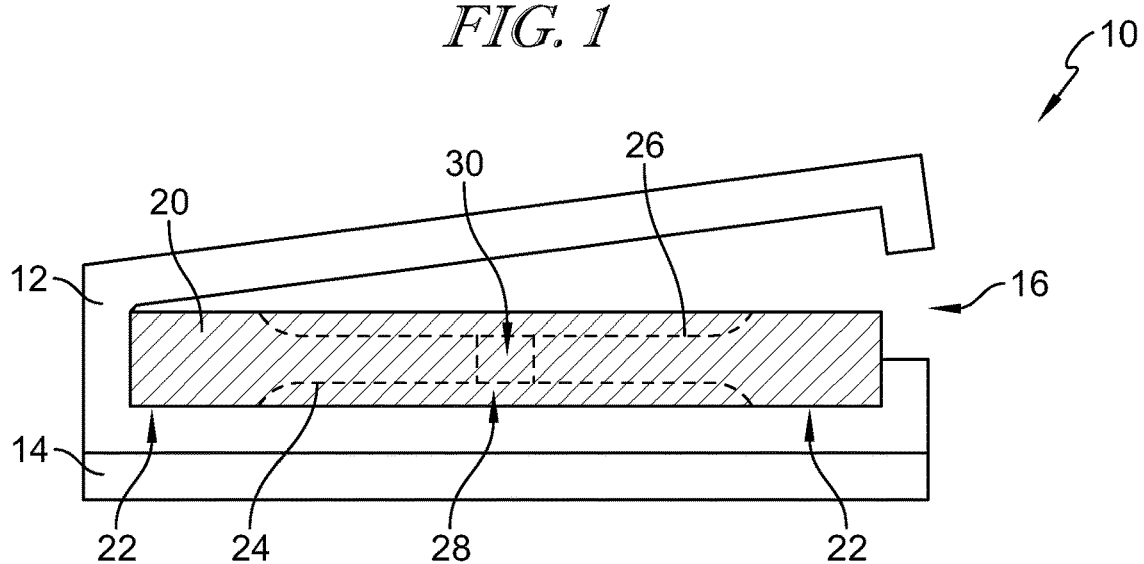
FIG. 2 is another cross-sectional side view of a first embodiment of a protective dressing of FIG. 1 with the opening in the open position, with a phase change material cooling insert inserted.
Figure 3:
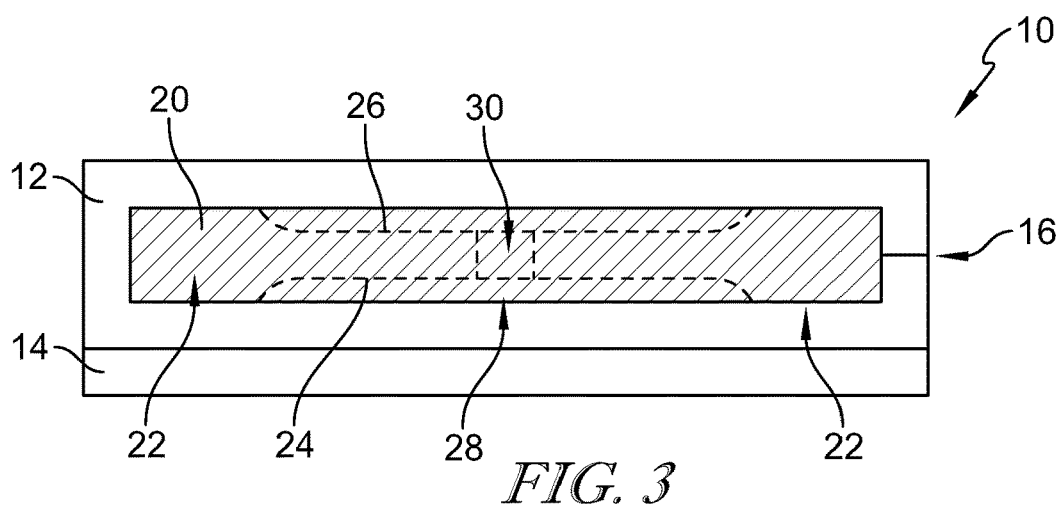
FIG. 3 is a cross-sectional side view of the protective dressing of FIG. 1 with the opening in the sealed position.

The barrier dressing 12 includes an opening 16. The opening 16 may be opened as shown in FIGS. 1 and 2 or sealed as shown in FIG. 3. The opening 16 may be self-sealing, for example using an adhesive or a hook-and-loop fastener. As best shown in FIG. 1, the opening 16 leads into an internal cavity 18 defined in the barrier dressing. As best shown in FIG. 2, when opened, the opening 16 is sized to allow a phase change material (PCM) cooling insert 20 to be inserted and/or removed from the barrier dressing 12. The cavity 18 is sized to receive the PCM insert 20 inserted through the opening 16. When inserted, the PCM insert 20 completely fill the cavity 18.

As shown in FIGS. 2 and 3, the PCM insert 20 is a removable encapsulated component that includes a phase change material. The phase change material may be embodied as any compound that changes its phase (e.g., from solid to liquid or from liquid to vapor) at a specific temperature. In some embodiments, the phase change material is included in a carrier medium such as an elastomer (in foam or non-foam form), a gel, or oil. The phase change material is embodied as a material with a melting temperature that is appropriate for focal cooling to prevent tissue damage, for example, to cool skin as much as possible without causing vasoconstriction at the application site. For example, a PCM insert 20 provides gentle cooling protection by maintaining skin temperature between 86° F. and 92° F. In another embodiment, a PCM insert 20 may provide extreme cooling protection by maintaining skin temperature, such as between 60° F. and 70° F. It should be understood that in some embodiments the protective dressing 10 may be used with PCM cooling inserts or with one or more PCM heating inserts, that is, a PCM insert configured for a higher stability temperature, such as between 100° F. and 105° F. to provide treatment to the skin.

In some embodiments, the phase change material may be embodied as one or more hexanes. Hexanes are simple chains of carbon and hydrogen that, depending upon chain length and bond configuration, have different temperatures at which they transition from the solid state to the liquid state. As another example, in some embodiments, the phase change material may be embodied as one or more anhydrous salts that reversibly bond to and release water at specific temperatures. In some embodiments, the protective dressing 10 may be used with multiple PCM inserts 20, which each may be configured for a particular stability temperature. For example the particular PCM or mix of PCMs in each PCM insert 20 may be adjusted to provide a range of stability temperatures.

The PCM insert 20 may have a thickness and/or compliance such that pressure exerted by the protective dressing 10 on the patient's skin does not significantly exceed the pressure exerted by a similar dressing without phase change material. For example, the PCM insert 20 has a thickness of less than about ½ inch. In other embodiments, the PCM insert 20 may include a compliant carrier medium such as elastomeric foam or gel. In some embodiments, the PCM insert 20 has a thickness of greater than ½ inch.

In some embodiments, the PCM insert 20 may have a variable thickness such as that shown in phantom in FIGS. 2 and 3. The PCM insert 20 may have an annular outer ring 22 with a concaved with a concave lower surface 24 and a concave upper surface 26. The concave surfaces 24 and 26 provides relief and allows the barrier dressing 12 and adhesive layer 14 to conform to the shape of the PCM insert 20. The space 28 formed by the concave surface 24 provides relief for a bony prominence on the patient or otherwise provides relief for a wound which the protective dressing 10 overlies. In addition, the PCM insert 20 may further include an annular opening 30 between the surfaces 24 and 26 which provides further relief for a prominence or irregularity in the patient's skin. In some embodiments, only the lower concave surface 24 is present to provide relief and the upper concave surface 26 is omitted. The use of a annular PCM insert 20 or other shape that provides clearance is to distribute the load and any pressure that is transferred to the patient through the protective dressing 10 away from the wound or prominence to further reduce the potential for injury to the patient.

Figure 4:
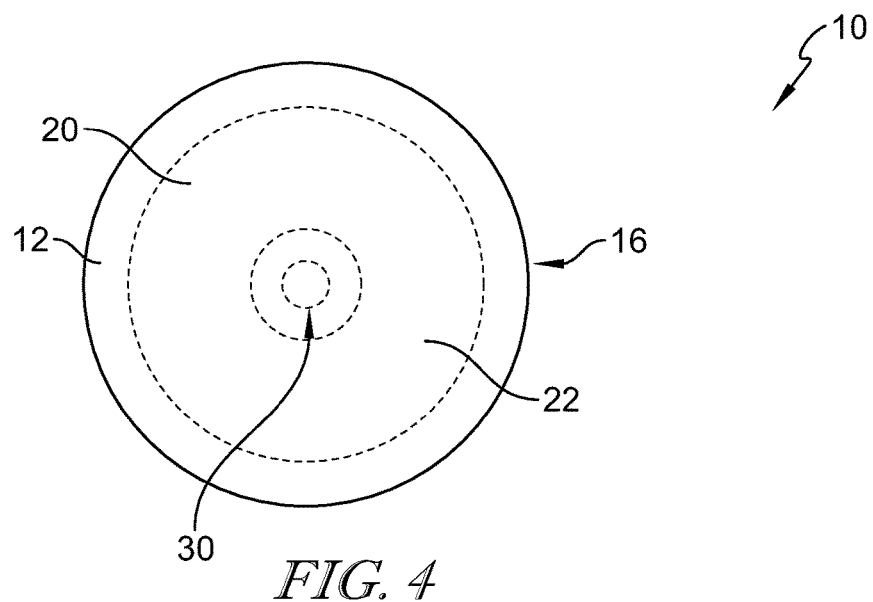
FIG. 4 is a top view of the protective dressing of FIG. 1.

Referring now to FIG. 4, a top view of the protective dressing 10 is shown. As illustrated, the barrier dressing 12 forms the top surface of the protective dressing 10 and the PCM insert 20 is positioned inside the protective dressing 10. In the illustrative embodiment, the opening 16 is positioned on a side of the protective dressing 10. The protective dressing 10 may have any appropriate shape and/or size to fit the PCM insert 20. Illustratively, the protective dressing 10 as shown in FIG. 4 is circular with a diameter of about three inches. As another example, in some embodiments, the protective dressing 10 may have a roughly cardioid shape suitable to be applied to the patient's sacral area and may have sides of about three inches long.

Illustratively, in use the protective dressing 10 provides preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a protective dressing 10 having an appropriate size and stability temperature for the patient and the vulnerable area. The healthcare provider may attach the protective dressing 10 to the vulnerable site using the adhesive layer 14.

The healthcare provider may select a PCM insert 20 having an appropriate stability temperature for the patient and the vulnerable area. For example, in some embodiments the healthcare provider may select a PCM insert 20 from several PCM inserts 20 kept in a refrigerated storage. The PCM inserts 20 may be refrigerated to a temperature below the lowest stability temperature of the PCM inserts 20 to ensure that all of the PCM inserts 20 are stored in the solid phase and ready to be used for patient cooling. In use, the healthcare provider inserts the selected PCM insert 20 into the protective dressing 10 through the opening 16.

After a PCM insert 20 warms beyond its stability temperature, the PCM insert 20 is removed and another, refrigerated PCM insert 20 is inserted into the protective dressing 10. The PCM insert 20 may be reused, and the rest of the protective dressing 10 (e.g., the barrier dressing 12 and the adhesive layer 14) may be disposable after a period of use or after a particular patient's treatment concludes.

Figure 5:
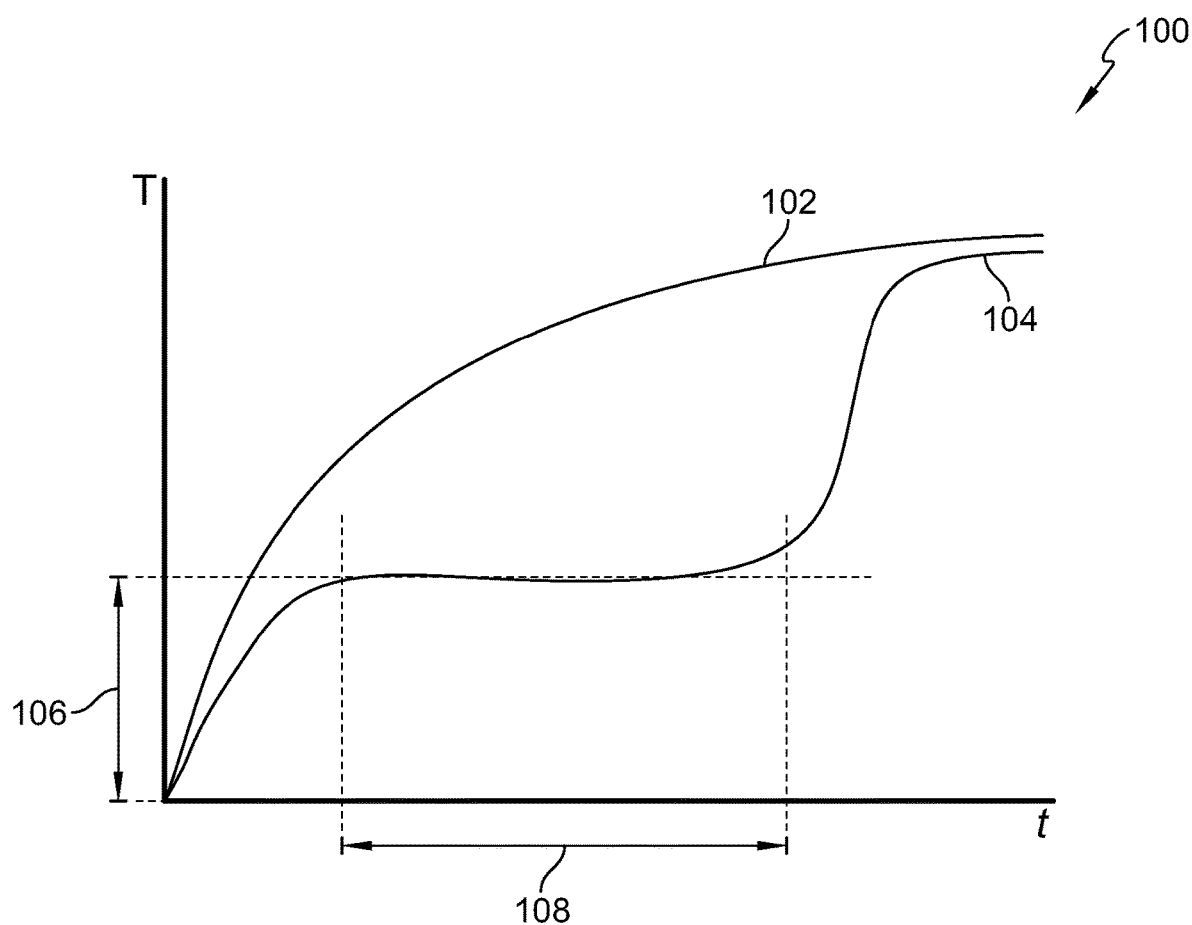
FIG. 5 is a plot illustrating temperature change that may be achieved with the protective dressing of FIG. 1.

Referring now to FIG. 5, the plot 100 illustrates potential cooling that may be achieved using the protective dressing 10. The curve 102 illustrates normal warming of the patient's skin that may occur without the application of the protective dressing 10. The curve 104 illustrates the temperature of the surface of the protective dressing 10. The protective dressing 10 may withdraw heat from the patient's skin as long as the temperature of the surface of the protective dressing 10 is less than the temperature of the patient's skin. Thus, the curve 104 illustrates one example of the cooling effect of the protective dressing 10. As shown, the temperature of the protective dressing 10 increases until reaching the stability temperature 106, which corresponds to the melting temperature of the phase change material within the PCM insert 20. The temperature of the protective dressing 10 remains near the stability temperature 106 for a stability duration 108. During the stability duration 108, the phase change material may be partially melted and thus remains near the melting temperature. The length of the duration 108 depends on the concentration of phase change material that is near the surface of the protective dressing 10 and also on the stability temperature 106 and thus near the patient's skin. In many embodiments of the protective dressing 10, the stability duration 108 may be at least two hours long. After the end of the stability duration 108, for example, after all of the phase change material has melted the temperature of the protective dressing 10 increases similarly to a normal dressing without the phase change material.

The shape of the curve 104 may be influenced by several factors, including the conductivity and the specific heat of the phase change material and/or the carrier medium. For example, increasing the heat conductivity of the carrier medium causes the "sharpness" of the curve 104 to increase; that is, with higher heat conductivity, the temperature of the protective dressing 10 increases from the initial value to the stability temperature 106 more quickly, remains closer to the stability temperature 106 during the stability duration 108, and increases more quickly after the stability duration 108 has ended. Similarly, the specific heat of the phase change material and the carrier medium affects the curve 104. For example, a higher ratio of heat energy going into phase change rather than into temperature change causes the sharpness of the curve 104 to increase, and a lower ratio causes sharpness to decrease and prolongs the warming phase.

Figure 6:
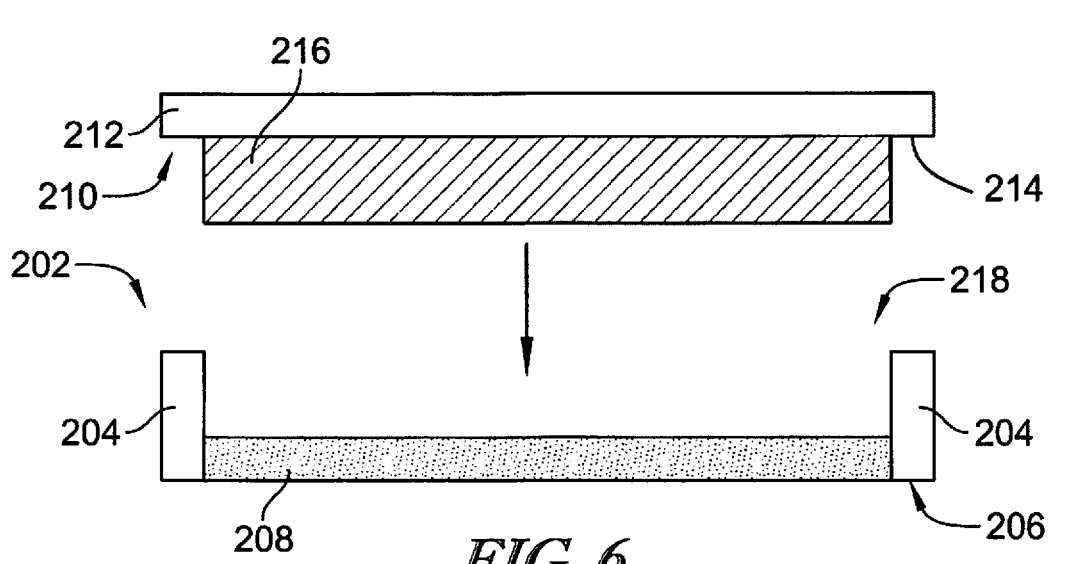
FIG. 6 is a cross-sectional side view of a second embodiment of a protective dressing with a phase change material cooling insert.
Figure 7:
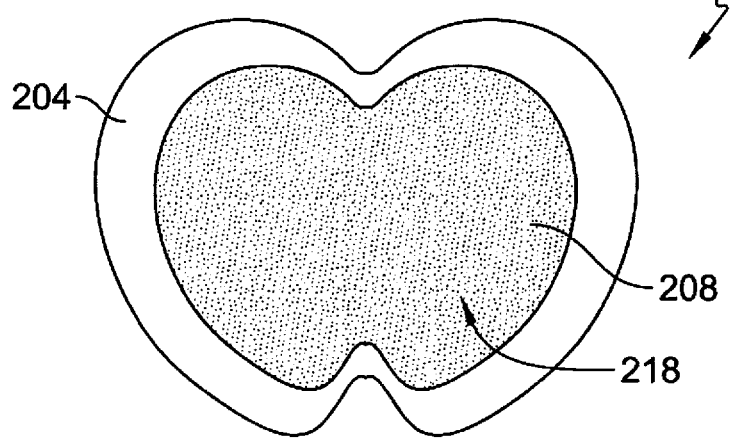
FIG. 7 is a top view of the protective dressing of FIG. 6 with an upper adhesive layer removed.
Figure 8:
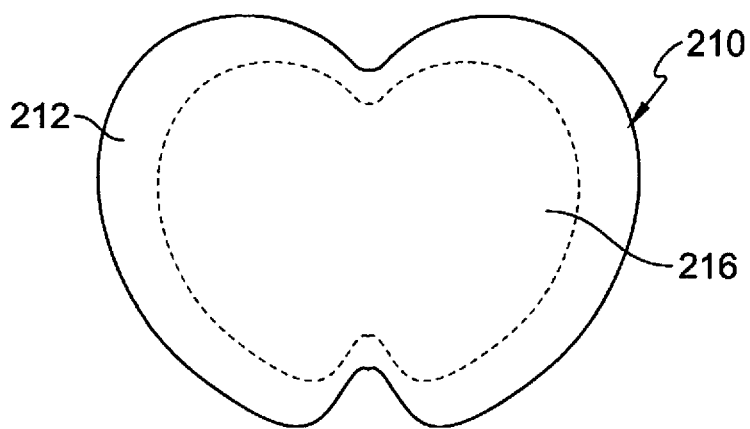
FIG. 8 is a top view of the protective dressing of FIG. 6.

Referring now to FIGS. 6-8, an illustrative protective dressing 200 includes a lower adhesive layer 202 and an upper adhesive layer 210. The lower adhesive layer 202, shown in FIGS. 6 and 7, includes a barrier dressing 204 and a foam layer 208. The barrier dressing 204, similar to the barrier dressing 12 of FIGS. 1-4, is a medical dressing or bandage, and may be impermeable to moisture and/or air.

The barrier dressing 204 is illustratively constructed of soft, compliant material with layers that slide readily over one another so that the protective dressing 200 imposes limited pressure and shear to the vulnerable site. The barrier dressing 204 includes an adhesive lower surface 206, which may be embodied as any adhesive coating or adhesive layer capable of adhering the lower adhesive layer 202 to the patient's skin. The foam layer 208 may be embodied as any elastomeric foam or other compliant material that cushions the patient's skin. As described below, the barrier dressing 204 and/or the upper adhesive layer 210 may retain the foam layer 208 within the protective dressing 200. In some embodiments, the lower adhesive layer 202 may remain on the patient's skin for the duration of hospitalization for acute care (e.g., four to five days).

The upper adhesive layer 210, shown in FIGS. 6 and 8, includes a barrier dressing 212 and a phase change material (PCM) cooling insert 216. The barrier dressing 212, similar to the barrier dressing 204 and the barrier dressing 12 of FIGS. 1-4, is a medical dressing or bandage, and may be impermeable to moisture and/or air. The barrier dressing 212 includes an adhesive lower surface 214, which may be embodied as any adhesive coating or adhesive layer capable of adhering the upper adhesive layer 210 to the lower adhesive layer 202. As described below, the upper adhesive layer 210 may be removed from the lower adhesive layer 202 periodically, for example to replace the PCM insert 216.

The PCM insert 216, similar to the PCM insert 20 of FIGS. 1, 2, and 4, may be embodied as any disk, package, or other removable component that includes a phase change material. The phase change material may be embodied as any compound that changes phase (e.g., from solid to liquid) at a specific temperature. In some embodiments, the phase change material may be included in a carrier medium such as an elastomer (in foam or non-foam form), a gel, or oil. The phase change material may be embodied as any material with a melting temperature that is appropriate for focal cooling to prevent tissue damage, for example, to cool skin as much as possible without causing vasoconstriction at the application site. For example, the PCM insert 216 may provide gentle protection by maintaining skin temperature, such as 86° F. and 92° F. In some embodiments, the PCM insert 216 may provide extreme protection by maintaining skin temperature, such as 60° F. and 70° F. In some embodiments, the phase change material may be embodied as one or more hexanes. As another example, in some embodiments, the phase change material may be embodied as one or more anhydrous salts.

The PCM insert 216 may have a thickness and/or compliance such that pressure exerted by the protective dressing 200 on the patient's skin does not significantly exceed the pressure exerted by a similar dressing without phase change material. For example, the PCM insert 216 may have a thickness of less than about ½ inch. In some embodiments, the PCM insert 216 may include a compliant carrier medium such as elastomeric foam or gel.

As shown in FIGS. 6 and 7, the lower adhesive layer 202 includes an opening 218 defined in the barrier dressing 204. The upper adhesive layer 212 may be adhered to the lower adhesive layer 202, with the PCM insert 216 passing through the opening 218. The barrier dressings 204, 212 may adhere together, retaining the PCM insert 216 and the foam layer 208 within the protective dressing 200.

As shown in FIGS. 7 and 8, the lower adhesive layer 202 and the upper adhesive layer 210 have corresponding shapes. Illustratively, the lower adhesive layer 202 and the upper adhesive layer 210 have an anatomical, roughly triangular shape that may be appropriate for use on the patient's sacral area. In other embodiments, the lower adhesive layer 202 and the upper adhesive layer 210 may have any appropriate shape, for example, a circular shape. Similarly, the foam layer 208, the opening 218, and the PCM insert 216 also have corresponding shapes.

Illustratively, in use the protective dressing 200 may provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a protective dressing 200 having an appropriate size and stability temperature for the patient and the vulnerable area. The healthcare provider may attach the lower adhesive layer 202 of the protective dressing 200 to the vulnerable site.

The healthcare provider may select a PCM insert 216 having an appropriate stability temperature for the patient and the vulnerable area. For example, in some embodiments the healthcare provider may select a PCM insert 216 from several PCM cooling inserts 216 kept in refrigerated storage. The healthcare provider may adhere the upper adhesive layer 210, including the selected PCM insert 216, onto the lower adhesive layer 202. After the PCM insert 216 warms beyond its stability temperature, the upper adhesive layer 210 may be removed and another upper adhesive layer 210, including a refrigerated PCM insert 216, may be adhered to the lower adhesive layer 202. In some embodiments, the PCM insert 216 may be reused and the upper barrier dressing 212 may be disposable. Additionally, or alternatively, in some embodiments the entire upper adhesive layer 210 may be disposable.

Figure 9:
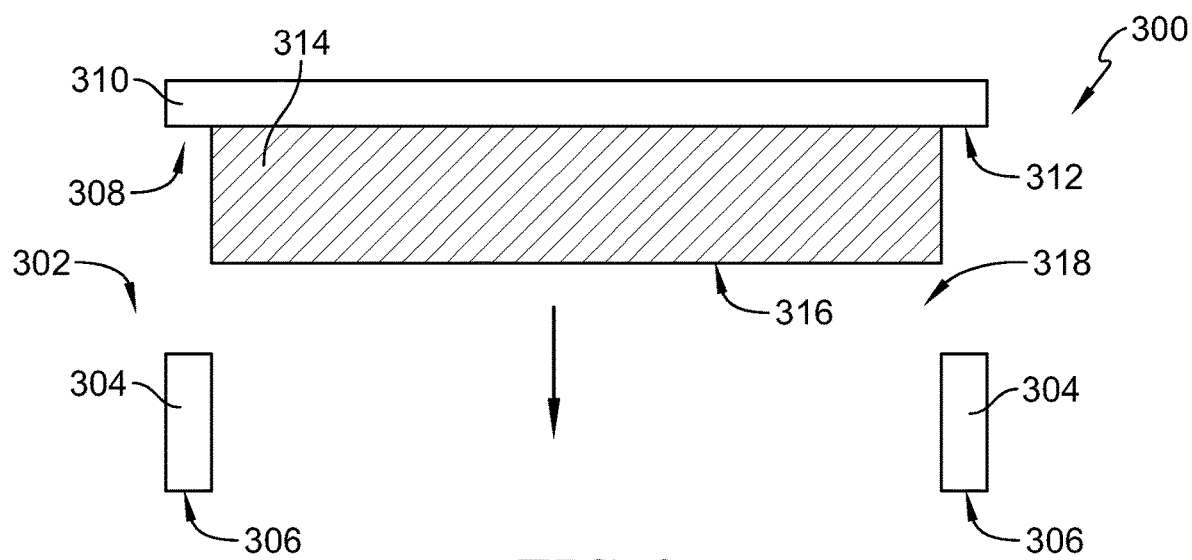
FIG. 9 is a cross-sectional side view of a third embodiment of a protective dressing with a phase change material cooling insert.
Figure 10:
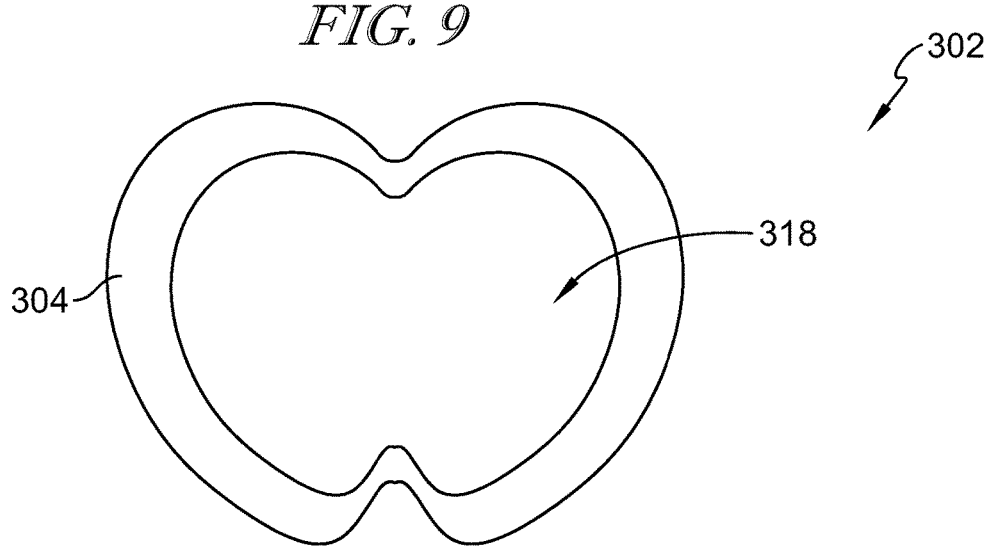
FIG. 10 is a top view of the protective dressing of FIG. 9 with an upper adhesive layer removed.
Figure 11:
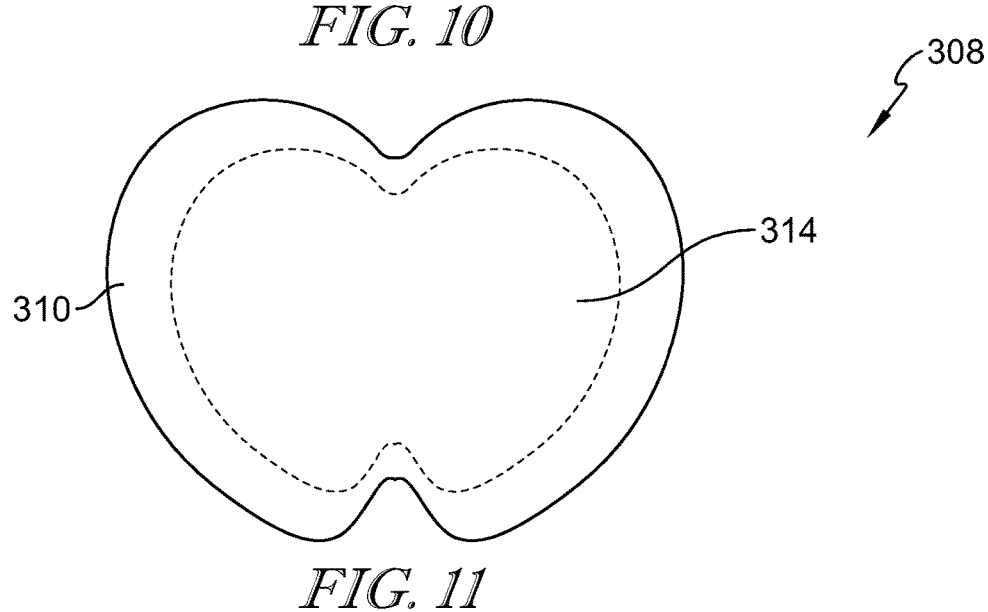
FIG. 11 is a top view of the protective dressing of FIG. 9.

Referring now to FIGS. 9-11, an illustrative protective dressing 300 includes a lower adhesive layer 302 and an upper adhesive layer 308. The lower adhesive layer 302, shown in FIGS. 9 and 10, includes a barrier dressing 304. The barrier dressing 304, similar to the barrier dressing 12 of FIGS. 1-4, is a medical dressing or bandage, and may be impermeable to moisture and/or air. The barrier dressing 304 may be constructed of soft, compliant material with layers that slide readily over one another so that the protective dressing 300 imposes limited pressure and shear to the vulnerable site. The barrier dressing 304 includes an adhesive lower surface 306, which may be embodied as any adhesive coating or adhesive layer capable of adhering the lower adhesive layer 302 to the patient's skin. In some embodiments, the lower adhesive layer 302 may remain on the patient's skin for the duration of hospitalization for acute care (e.g., four to five days).

The upper adhesive layer 308, shown in FIGS. 9 and 11, includes a barrier dressing 310 and a PCM insert 314. The barrier dressing 310, similar to the barrier dressing 304 and the barrier dressing 12 of FIGS. 1-4, is a medical dressing or bandage, and may be impermeable to moisture and/or air. The barrier dressing 310 includes an adhesive lower surface 312, which may be embodied as any adhesive coating or adhesive layer capable of adhering the upper adhesive layer 308 to the lower adhesive layer 302. As described below, the upper adhesive layer 308 may be removed from the lower adhesive layer 302 periodically, for example to replace the PCM insert 314.

The PCM insert 314, similar to the PCM insert 20 of FIGS. 1, 2, and 4, may be embodied as any disk, package, or other removable component that includes a phase change material included in a foam carrier medium. The phase change material may be embodied as any compound that changes phase (e.g., from solid to liquid) at a specific temperature. The phase change material is included in a foam carrier medium, such as an elastomeric foam. Thus, the PCM insert 314 includes a lower surface 316 which engages the patient's skin such that the PCM insert 314 cushions the patient's skin, similar to the foam layer 208 of FIGS. 6 and 7. The phase change material may be embodied as any material with a melting temperature that is appropriate for focal cooling to prevent tissue damage, for example, to cool skin as much as possible without causing vasoconstriction at the application site. For example, the PCM insert 314 may provide gentle protection by maintaining skin temperature, such as 86° F. and 92° F. In some embodiments, the PCM insert 314 may provide extreme protection by maintaining skin temperature, such as 60° F. and 70° F. In some embodiments, the phase change material may be embodied as one or more hexanes. As another example, in some embodiments, the phase change material may be embodied as one or more anhydrous salts.

As shown in FIGS. 9 and 10, the lower adhesive layer 302 includes an opening 318 defined in the barrier dressing 304. The upper adhesive layer 308 may be applied to the lower adhesive layer 302, with the PCM insert 314 passing through the opening 318. The barrier dressings 304, 310 may adhere together, retaining the PCM insert 314 within the protective dressing 300.

As shown in FIGS. 10 and 11, the lower adhesive layer 302 and the upper adhesive layer 308 have corresponding shapes. Illustratively, the lower adhesive layer 302 and the upper adhesive layer 308 have an anatomical, roughly cardioid shape that may be appropriate for use on the patient's sacral area. In other embodiments, the lower adhesive layer 302 and the upper adhesive layer 308 may have any appropriate shape, for example, a circular shape. Similarly, the opening 318 and the PCM insert 314 also have corresponding shapes. The PCM insert 314 may have a cross section that minimizes the pressure directly over an anatomical site similar to the optional relief surfaces discussed above with regard to protective dressing 10.

Illustratively, in use the protective dressing 300 may be used to provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a protective dressing 300 having an appropriate size and stability temperature for the patient and the vulnerable area. The healthcare provider may attach the lower adhesive layer 302 of the protective dressing 300 to the vulnerable site.

The healthcare provider may select a PCM insert 314 having an appropriate stability temperature for the patient and the vulnerable area. For example, in some embodiments the healthcare provider may select a PCM insert 314 from several PCM cooling inserts 314 kept in refrigerated storage. The healthcare provider may adhere the upper adhesive layer 308, including the PCM insert 314, onto the lower adhesive layer 302. After the PCM insert 314 warms beyond its stability temperature, the upper adhesive layer 308 may be removed and another upper adhesive layer 308, including a refrigerated PCM insert 314, may be adhered to the lower adhesive layer 302. In some embodiments, the PCM insert 314 may be reused and the upper barrier dressing 310 may be disposable. Additionally, or alternatively, in some embodiments the entire upper adhesive layer 308 may be disposable.

Figure 12:
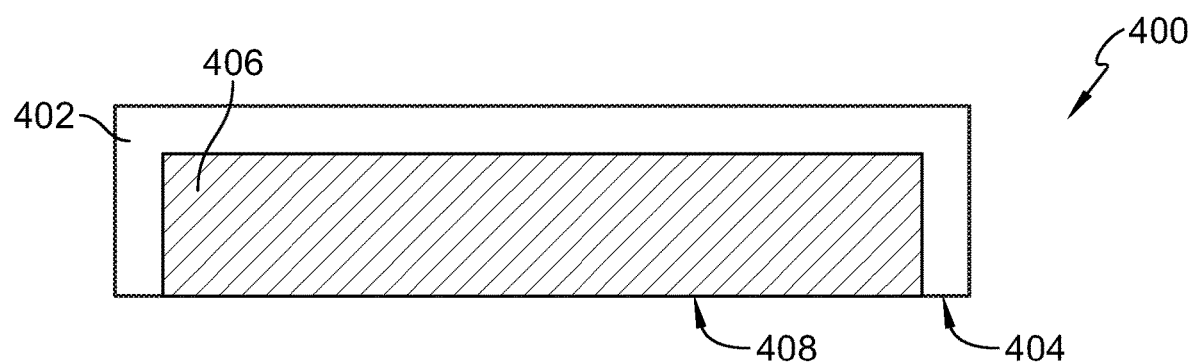
FIG. 12 is a cross-sectional side view of a fourth embodiment of a protective dressing with a phase change material cooling insert.
Figure 13:
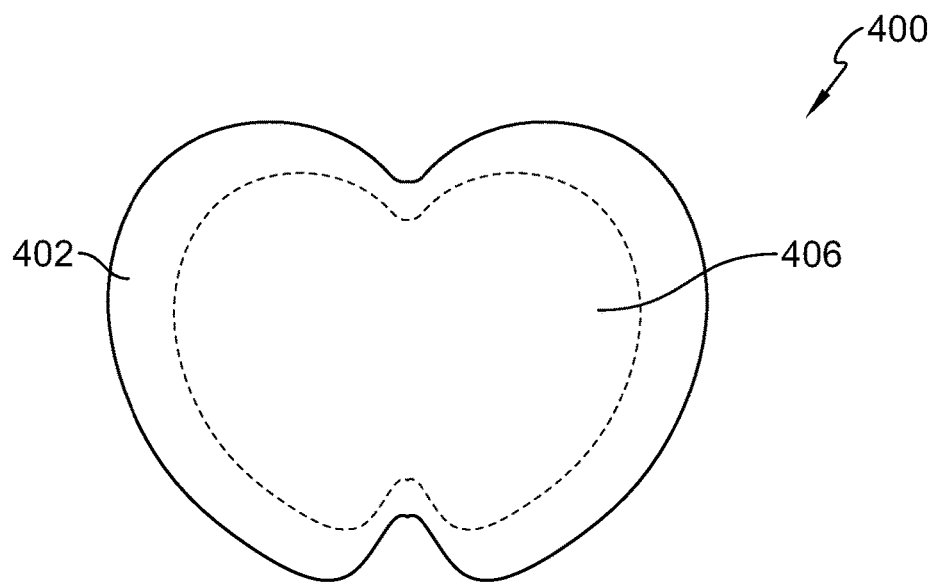
FIG. 13 is a top view of the protective dressing of FIG. 12.

Referring now to FIGS. 12 and 13, an illustrative protective dressing 400 includes a barrier dressing 402 and a PCM insert 406. The barrier dressing 402, similar to the barrier dressing 12 of FIGS. 1-4, is a medical dressing or bandage, and may be impermeable to moisture and/or air. The barrier dressing 402 may be constructed of soft, compliant material with layers that slide readily over one another so that the protective dressing 400 imposes limited pressure and shear to the vulnerable site. The barrier dressing 402 includes an adhesive lower surface 404, which may be embodied as any adhesive coating or adhesive layer capable of adhering the barrier dressing 402 to the patient's skin. In some embodiments, the barrier dressing 402 may remain on the patient's skin for the duration of hospitalization for acute care (e.g., four to five days).

The PCM insert 406, similar to the PCM insert 314 of FIGS. 9 and 11, may be embodied as any disk, package, or other component that includes a phase change material included in a foam carrier medium. The phase change material may be embodied as any compound that changes phase (e.g., from solid to liquid) at a specific temperature. The phase change material is included in a foam carrier medium, such as an elastomeric foam. Thus, the PCM insert 406 includes a lower surface 408 that engages the patient's skin such that the PCM insert 406 cushions the patient's skin, similar to the foam layer 208 of FIGS. 6 and 7. In some embodiments, the cross section of PCM insert 406 may be thinned for the portion to be directly over the anatomical area so as to reduce the pressure at the anatomical area. The phase change material may be embodied as any material with a melting temperature that is appropriate for focal cooling to prevent tissue damage, for example, to cool skin as much as possible without causing vasoconstriction at the application site. For example, the PCM insert 406 may provide gentle protection by maintaining skin temperature, such as 86° F. and 92° F. In some embodiments, the PCM insert 406 may provide extreme protection by maintaining skin temperature, such as 60° F. and 70° F. In some embodiments, the phase change material may be embodied as one or more hexanes. As another example, in some embodiments, the phase change material may be embodied as one or more anhydrous salts.

As shown in FIG. 13, the illustrative protective dressing 400 has an anatomical, roughly cardioid shape that may be appropriate for use on the patient's sacral area. In other embodiments, the protective dressing 400 may have any appropriate shape, for example, a circular shape.

Illustratively, in use the protective dressing 400 may be used to provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a protective dressing 400 having an appropriate size and stability temperature for the patient and the vulnerable area. In some embodiments, the healthcare provider may select a protective dressing 400 having a PCM insert 406 with an appropriate stability temperature for the patient and the vulnerable area. For example, in some embodiments the healthcare provider may select a protective dressing 400 from several protective dressings 400 kept in refrigerated storage. The healthcare provider may attach the barrier dressing 402 of the protective dressing 400 to the vulnerable site. After the PCM insert 406 warms beyond its stability temperature, protective dressing 400 continues to protect the vulnerable site from moisture, friction, and shear. In some embodiments, after the PCM insert 406 warms beyond its stability temperature, the protective dressing 400 may be disposed and/or replaced with another protective dressing 400.

Figure 14:
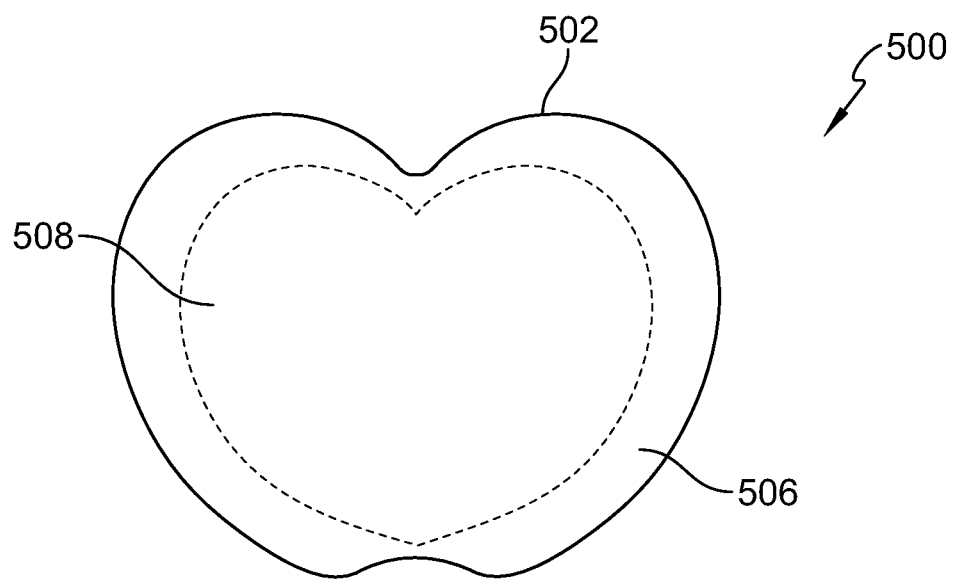
FIG. 14 is a top view of a fifth embodiment of a protective dressing with a phase change material cooling insert.
Figure 15:
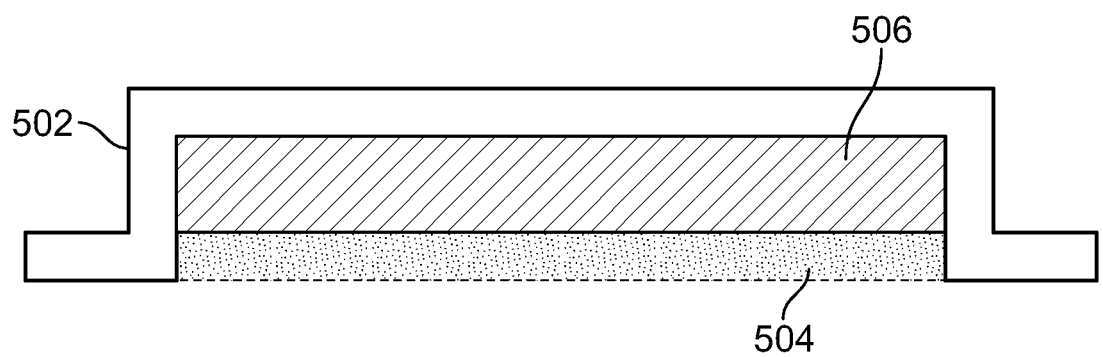
FIG. 15 is a cross-sectional side view of the protective dressing of FIG. 14.
Figure 16:
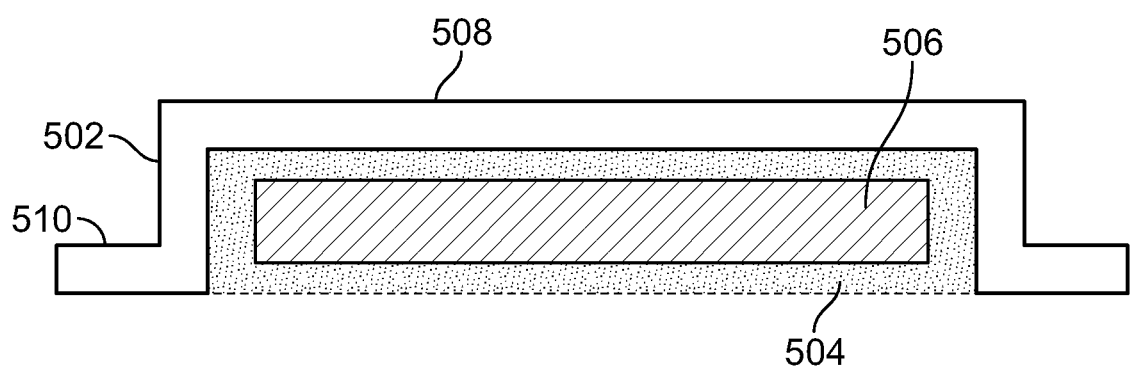
FIG. 16 is a cross-sectional side view similar to FIG. 15 showing an alternative embodiment of the protective dressing of FIG. 14.

Referring now to FIGS. 14-16, an illustrative disposable protective dressing 500 includes an outer adhesive layer 502, a cushion layer 504, and a PCM insert 506. The outer adhesive layer 502 includes an outer rim portion 510 and an upper portion 508. The outer rim portion 510 is configured to directly contact and adhere to the patient's skin. The outer rim portion 510 may be impermeable to moisture and/or vapor. The thermal conductivity of cushion layer 504 may be adjusted to provide different amounts of thermal flux for a given PCM insert 506.

The upper portion 508 is configured to retain the PCM insert 506 and the cushion layer 504 between the outer adhesive layer 502 and the patient's skin. In one embodiment, as shown in FIG. 15, the PCM insert 506 may be positioned between the cushion layer 504 and the outer adhesive layer 502. In other embodiment, as shown in FIG. 16, the PCM insert 506 may be positioned within the cushion layer 504. The cushion layer 504 may be embodied as any elastomeric foam or other compliant material that cushions the patient's skin. As shown in FIG. 14, the illustrative protective dressing 500 has an anatomical, roughly cardioid shape that may be appropriate for use on the patient's sacral area. In other embodiments, the protective dressing 500 may have any appropriate shape, for example, a circular shape.

The phase change material may be embodied as any material with a melting temperature that is appropriate for focal cooling to prevent tissue damage, for example, to cool skin as much as possible without causing vasoconstriction at the application site. For example, the PCM insert 506 may provide gentle protection by maintaining skin temperature, such as 86° F. and 92° F. In some embodiments, the PCM insert 506 may provide extreme protection by maintaining skin temperature, such as 60° F. and 70° F. In some embodiments, the phase change material may be embodied as one or more hexanes. As another example, in some embodiments, the phase change material may be embodied as one or more anhydrous salts.

Illustratively, in use the protective dressing 500 may provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a protective dressing 500 having an appropriate size and stability temperature for the patient and the vulnerable area. The healthcare provider may attach the protective dressing 500 to the vulnerable site.

The healthcare provider may select a protective dressing 500 that has a PCM insert 506 with an appropriate stability temperature for the patient and the vulnerable area. For example, in some embodiments the healthcare provider may select a protective dressing 500 from several protective dressings 500 kept in refrigerated storage. The healthcare provider may adhere the protective dressing 500, including the selected PCM insert 506, onto the patient's vulnerable site. For example, a phase change material of the PCM insert 506 may be in a liquid phase to prevent increasing the interface pressure against the patient's skin. In such embodiment, after the PCM insert 506 warms beyond its stability temperature, the liquid phase change material changes to a vapor phase. When the temperature of the PCM insert 506 becomes the same as the temperature of the patient's skin, the protective dressing 500 may remain on the patient or may be removed and disposed.

Although described as a PCM insert 506, it should be understood that in some embodiments the protective dressing 500 may be used with one or more PCM heating inserts, that is, a PCM insert configured for a higher stability temperature, such as between 100° F. and 105° F. to provide treatment to the skin.

Referring now to FIGS. 17-22, FIGS. 17-22 illustrate different embodiments that incorporate thermally conductive heat transfer to dissipate and remove the heat from the patient's skin or to provide heat to the patient's skin, which will be described in detail below. Thermally conductive heat transfer makes use of a heat gradient to transfer heat from an area of high heat to an area of lower heat.

Figure 17:
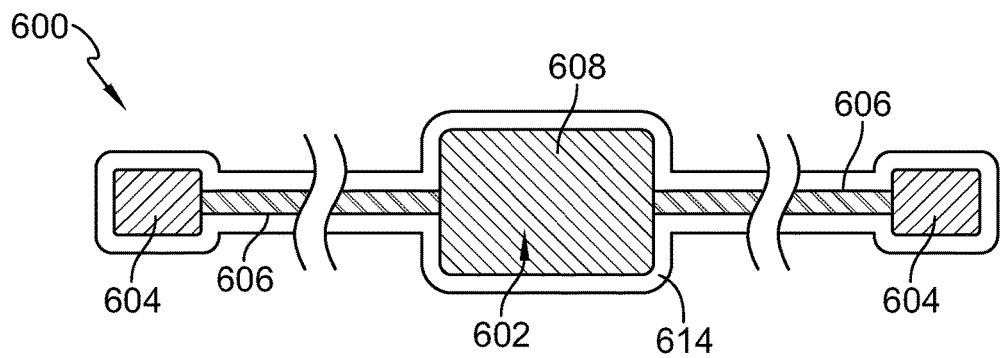
FIG. 17 is a cross-sectional top view of a thermally conductive apparatus.
Figure 18:
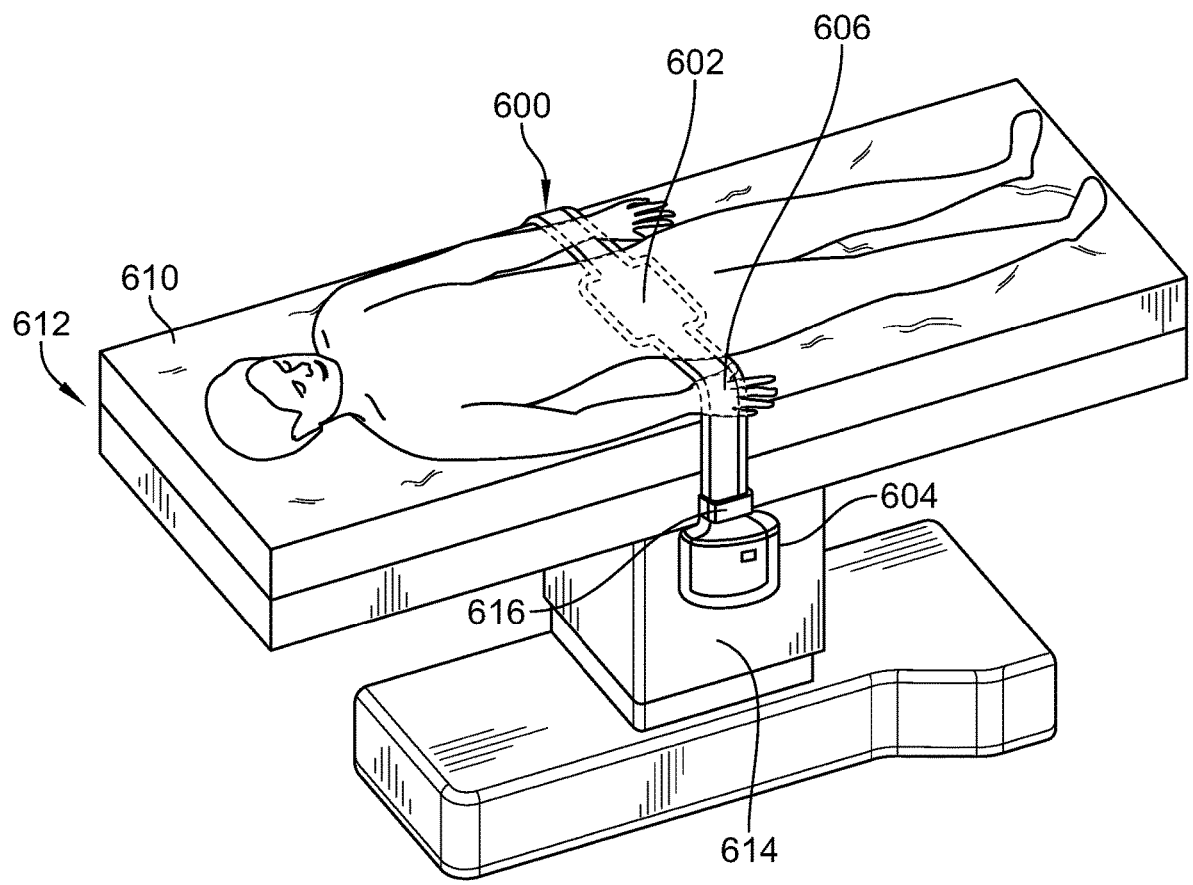
FIG. 18 is a perspective view from a head end on the patient's right of a patient support apparatus of the thermally conductive apparatus of FIG. 17 coupled to the patient support apparatus.

In some embodiments, as shown in FIGS. 17 and 18, a thermally conductive apparatus 600 is used to conduct heat away from an area of the patient's body that is in contact with the thermally conductive apparatus 600, and thereby reduces the risk of pressure ulcers. The thermally conductive apparatus 600 includes a conductive pad 602, compartment portions 604 on each side of the conductive pad 602, conductive conduits 606 connecting the compartment portions 604 to the conductive pad 602, and an outer layer 614. The outer layer 614 is designed to encase the conductive pad 602, the conductive conduits 606, and compartment portions 604. Each compartment portion 604 includes an opening (not shown) configured to receive a heat sink, which will be described in detail below. In some embodiments, the thermally conductive apparatus 600 may include one compartment portion 604.

The conductive pad 602 is designed to underlie the patient's pelvic region, particularly under the sacrum, to withdraw the heat from that region. It should be appreciated that the conductive pad 602 may be sized to underlie a smaller area of the patient's body where the heat withdrawal is needed. The conductive pad 602 is made of a heat conducting material 608. The heat conducting material 608 may be any material that is capable of conducting heat, for example, a copper, carbon fiber, or graphene. The compartment portion 604 and the conductive conduit 606 are also made of a heat conducting material capable of conducting heat, for example, a copper, carbon fiber, or graphene. The heat conducting material of the compartment portion 604 may be extension of the conductive conduit 606. In some embodiments, the conductive pad may also include an adhesive layer and a cushion layer. In such embodiments, the heat conducting material may be embedded in the cushion layer or embedded between the cushion layer and the outer adhesive layer.

As shown in FIG. 18, the compartment portion 604 is positioned on each side of the conductive pad 602 and is connected via the conductive conduits 606. The thermally conductive apparatus 600 may further include a fastener 616 to temporarily attach the conductive conduits 606 to a patient support apparatus 612. The fastener 616 is detachable from the patient support apparatus 612 and repositionable on the patient support apparatus 612 in order to position the conductive pad 602 underneath the particular patient's anatomic region. When the conductive pad 602 is positioned underneath the patient supported on a surface 610 of the patient support apparatus 612, the compartment portion 604 is designed to rest below a surface 610 of a patient support apparatus 612, such that the compartment portion 604 is hanging on each side of the patient support apparatus 612. The compartment portion 604 is configured to receive a removable heat sink, for example, a PCM cooling insert, an ice pack, or other material that will drive a chemical endothermic reaction to withdraw the heat.

Illustratively, in use the thermally conductive apparatus 600 may provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a heat sink having an appropriate size and stability temperature for the patient and the vulnerable area. In such an embodiment, the removable heat sink may be replaceable without removing the entire thermally conductive apparatus 600 from the patient's body. Once the removable heat sink is received in the compartment 604, the removable heat sink maintains the cool temperature to withdraw the heat from the conductive pad 602 underneath the patient's skin, thereby withdrawing the heat away from the patient's skin.

Although described as providing focal cooling of the vulnerable site, it should be understood that in some embodiments the thermally conductive apparatus 600 may be used with one or more PCM heating inserts, that is, a PCM insert configured for a higher stability temperature, such as between 100° F. and 105° F. to provide treatment to the skin. In this embodiment, the PCM insert is the area of higher heat and heat flows from the PCM insert to the conductive pad 602.

It should be appreciated that, in some embodiments, a thermally conductive apparatus includes a conductive pad and a conductive conduit, which is directly coupled to a frame 614 of the patient support apparatus 612. In such embodiment, the frame 614 acts as a large volume of heat sink. In other embodiments, a thermally conductive apparatus may include a conductive pad and a conductive conduit that has finger-like projections at a free-end of the conductive conduit such that the projections are exposed to the ambient air temperature to increase the surface area to drive the heat exchange.

Figure 19:
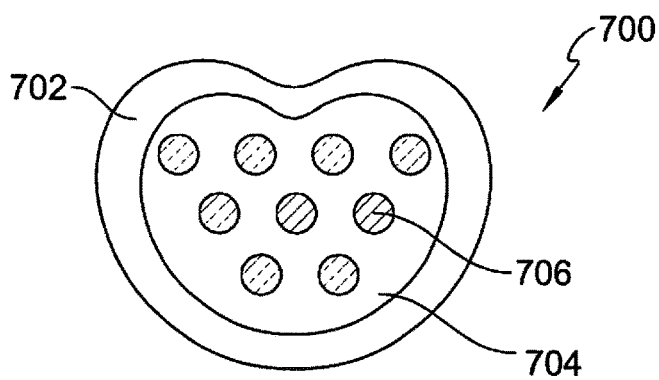
FIG. 19 is a cross-sectional top view of a thermally conductive pad.
Figure 20:
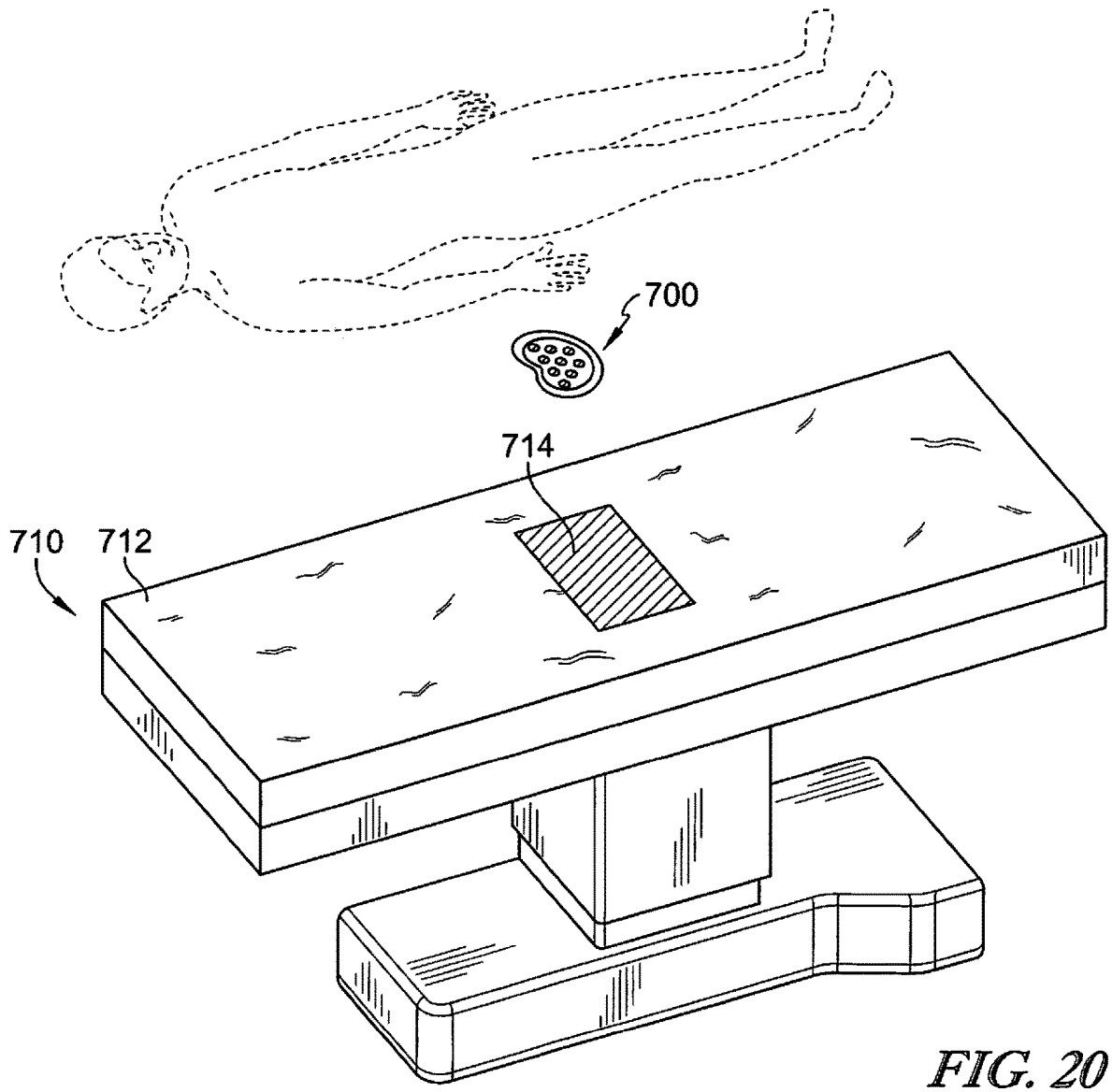
FIG. 20 is a perspective view from a head end on the patient's right of a patient support apparatus of the thermally conductive pad of FIG. 19 coupled to the patient support apparatus.

In some embodiments, a conductive pad may be directly coupled to a patient support apparatus. For example, as shown in FIGS. 19 and 20, a thermally conductive pad 700 is directly coupled to a patient support apparatus 710. The thermally conductive pad 700 may include an outer adhesive layer 702, a cushion layer 704, and a plurality of thermally conductive regions 706. The surface 712 of the patient support apparatus 710 also includes a thermally conductive region 714 that is configured to contact the thermally conductive regions 706 of the thermally conductive pad 700. The thermally conductive region 714 acts as a heat sink to withdraw heat from the thermally conductive region 706.

Figure 21:
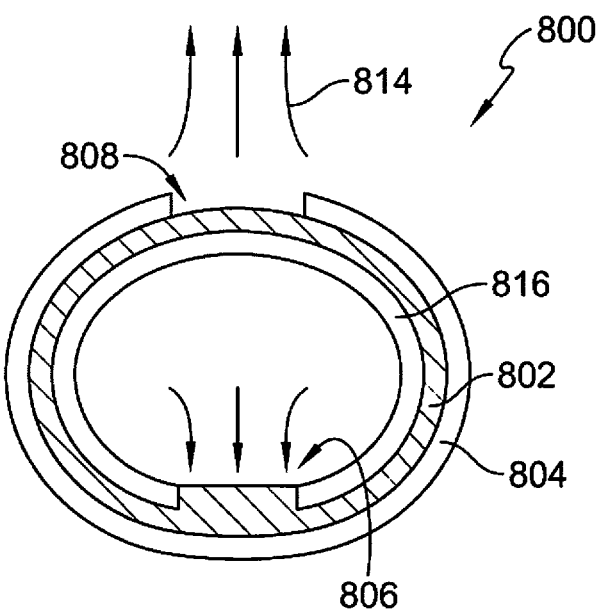
FIG. 21 is a cross-sectional side view of a wearable conductive strap.
Figure 22:
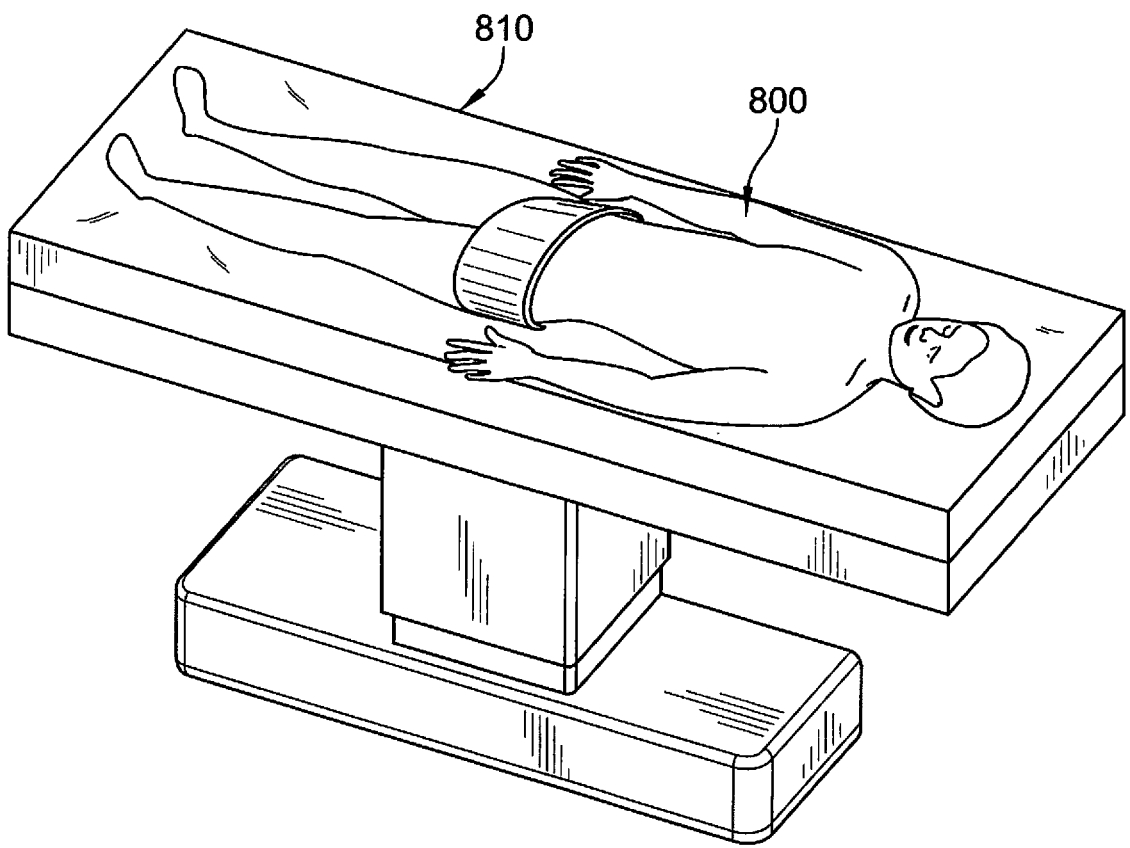
FIG. 22 is a perspective view from a foot end on the patient's right of a patient support apparatus of the wearable conductive strap of FIG. 21 coupled to the patient support apparatus.

Referring now to FIGS. 21 and 22, a wearable conductive strap 800 is shown. As shown in FIG. 22, the wearable conductive strap 800 is design to wrap around a patient's torso. As shown in FIG. 21, the wearable conductive strap 800 includes a flexible heat conducting material 802, such as thermally conductive fibers, an inner non-conductive insulated layer 816, and an outer non-conductive insulated layer 804. The thermally conductive fibers 802 are designed to be insulated between the inner non-conductive insulated layer 816 and the outer non-conductive insulated layer 804, except at two openings 806, 808. The first opening 806 is positioned at the inner non-conductive insulated layer 816 facing the patient's skin such that the thermally conductive fibers 802 are in contact with the patient's skin at the first opening 806. The second opening 808 is positioned at the outer non-conductive insulated layer 804 facing ambient air such that the thermally conductive fibers 802 is exposed to ambient air.

As shown in FIG. 22, in use the first opening 806 is configured to underlie a pelvic region of a patient lying supine on the patient support apparatus 810, while the second opening 808 is configured to be positioned opposite the first opening 806 on the ventral side of the patient. The conductive fibers 802 at the second opening 808 are exposed to the air and convectively transfer the heat to the air in the direction of arrows 814.

For example, an interface between the patient support apparatus 810 and the patient's pelvic region is prone to develop pressure ulcer. By positioning the first opening 806 underneath the pelvic region, it allows the conductive fibers 802 to withdraw heat from the patient's body by conducting heat from the first opening 806 and direct it towards the second opening 808, where the surrounding air is typically cooler than the first opening 806. The heat is then released at the second opening 808.

It should be appreciated that the wearable conductive strap 800 may be used to warp around other anatomic location of the patient's body. In some embodiments, the wearable conductive strap 800 may lie flat on the patient support apparatus, similar to the thermally conductive apparatus 600 shown in FIGS. 17 and 18. Such an embodiment includes a first opening positioned underneath the pelvic region of the patient lying supine on the patient support apparatus and a second opening positioned at the side of the patient but not in contact with the patient's body. In some embodiments, the wearable conductive strap may include two second openings at each side of the patient, thereby increasing surface areas that are exposed to air.

Figure 23:
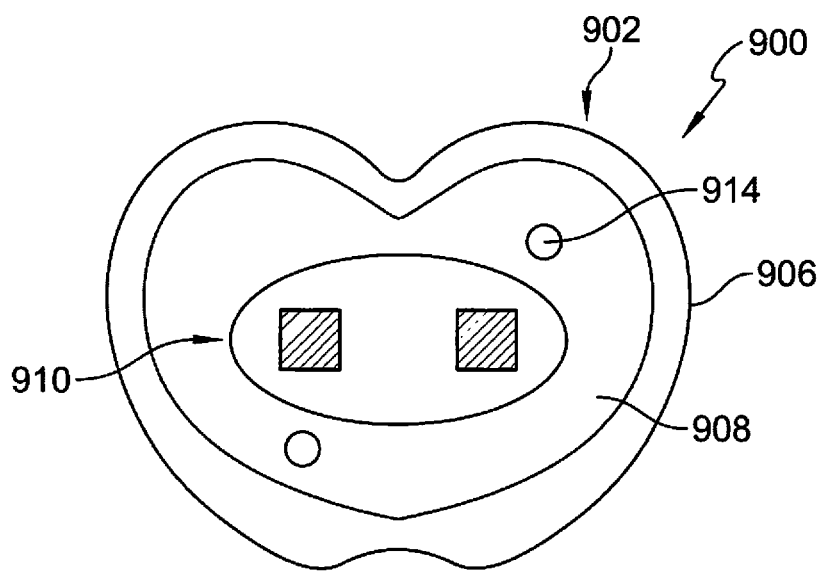
FIG. 23 is a cross-sectional side view of a thermoelectric device.
Figure 24:
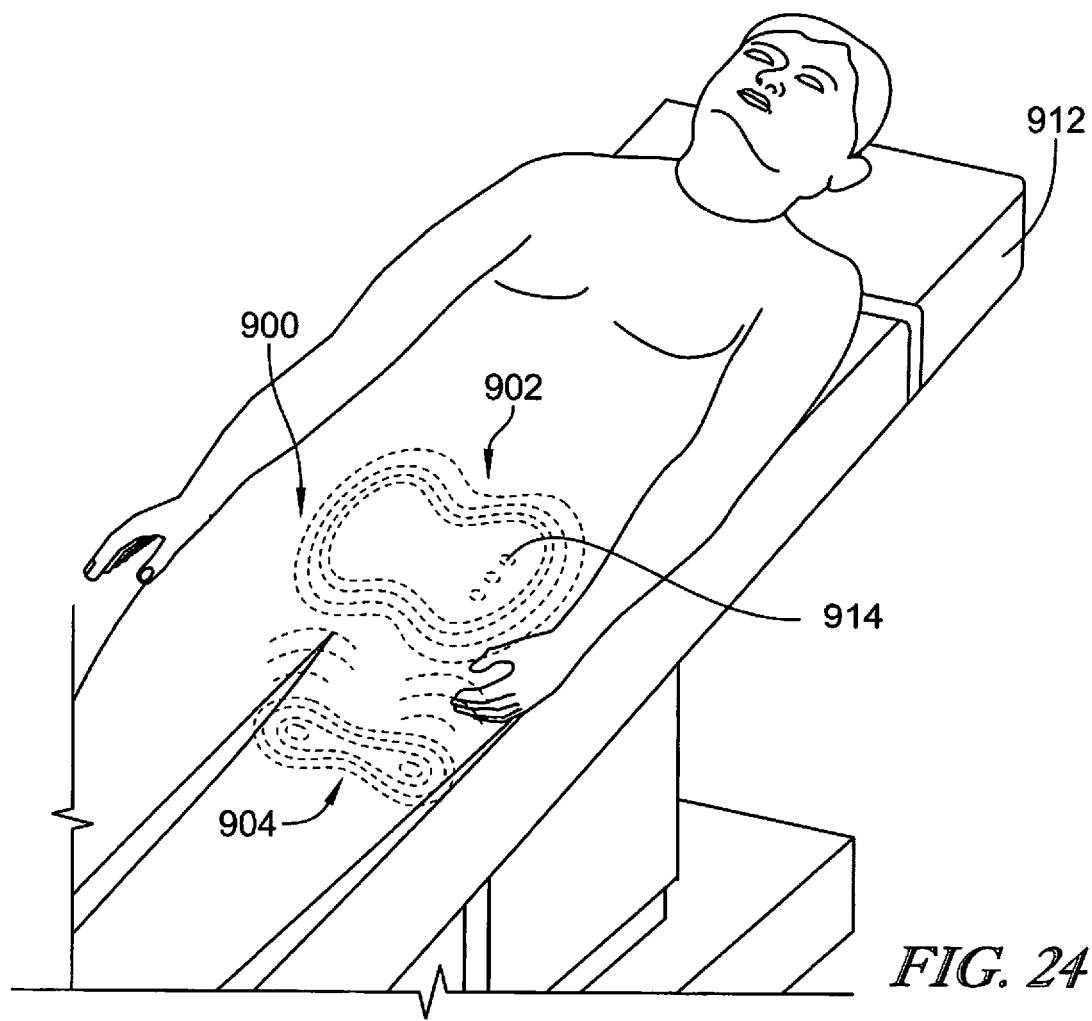
FIG. 24 is a perspective view of the thermoelectric device of FIG. 23 coupled to a patient support surface.

Referring now to FIGS. 23 and 24, a thermoelectric device 900 for focal cooling and heating is shown. The thermoelectric device 900 includes a thermoelectric pad 902 and a power source 904. The thermoelectric pad 902 includes an outer adhesive layer 906, a cushion layer 908, a thermoelectric module 910, and a plurality of sensors 914. The thermoelectric module 910 may be integrated between the outer adhesive layer 906 and the cushion layer 908 or may be embedded in the cushion layer 908. As shown in FIG. 24, the power source 904 is integrated into a patient support apparatus 912. The thermoelectric module 910 is configured to inductively couple to the power source 904 such that the module 910 receives electrical power wirelessly from the power source 904. In some embodiments, the power source may be positioned in close proximity to the thermoelectric module. In other embodiments, the thermoelectric module may be directly connected to the external power source via a wire to receive electrical power.

The thermoelectric module 910 is a solid state device that uses the Peltier effect to transfer heat between first and second sides depending on a polarity of current. The thermoelectric module 910 converts electrical energy from the power source 904 into a thermal gradient. Specifically, when a power source 904 applies a voltage to the thermoelectric module 910, one side of the thermoelectric module 910 becomes cooler and is referred to as a "cold side"; the other side of the thermoelectric module becomes warmer and is referred to as a "hot side." The cold side and hot side are determined by the polarity of the thermoelectric module 910, and the polarity may be reversed by changing the direction of current flow. In other words, depending on the direction of current flow, the thermoelectric device 900 may be used for either cooling the patient's skin for prevention of pressure ulcers or warming the patient's skin to treat existing ulcers, other wounds, pain management, and peripheral neuropathy.

When the thermoelectric device 900 is used for prevention of pressure ulcers, the cold side of a thermoelectric module 910 is configured to contact the patient's skin, and the hot side of the thermoelectric module 910 is configured to communicate with a heat sink, which in FIG. 24 is a patient support apparatus 912. In some embodiments, the heat sink may be ambient air. In other embodiments, a thermally conductive path may create a thermal circuit from the thermoelectric module to a heat sink. On the other hand, when the thermoelectric device 900 is used for treatment, the hot side of the thermoelectric module 910 is configured to contact the patient's skin, and the cold side of the thermoelectric module 910 is configured to face the patient support apparatus 912.

The sensors 914 are, for example, pressure, temperature, and/or moisture sensors configured to detect conditions of the patient's skin where the thermoelectric module 910 is positioned and provide feedback to caregivers. Depending on the condition of the patient's skin, the caregivers may determine a position and duration of the thermoelectric module 910 on the patient's skin to withdraw or provide heat, thereby providing efficient prevention or treatment for pressure ulcers.

In some embodiments, the sensor 914 may provide feedback to the thermoelectric module 910 to control the direction of the current flow. For example, temperature sensors are configured to determine the temperature of the patient's skin. If the temperature exceeds a first threshold, the thermoelectric module 910 is activated to allow the cold side to be in contact with the patient's skin to remove heat. On the other hand, if the temperature is below a second threshold, the thermoelectric module 910 is activated to allow the hot side to be in contact with the patient's skin to provide heat. Sensors may detect onset of DTI, blood flow, movement or other parameter to provide feedback control to thermoelectric module 910.

Figure 25:
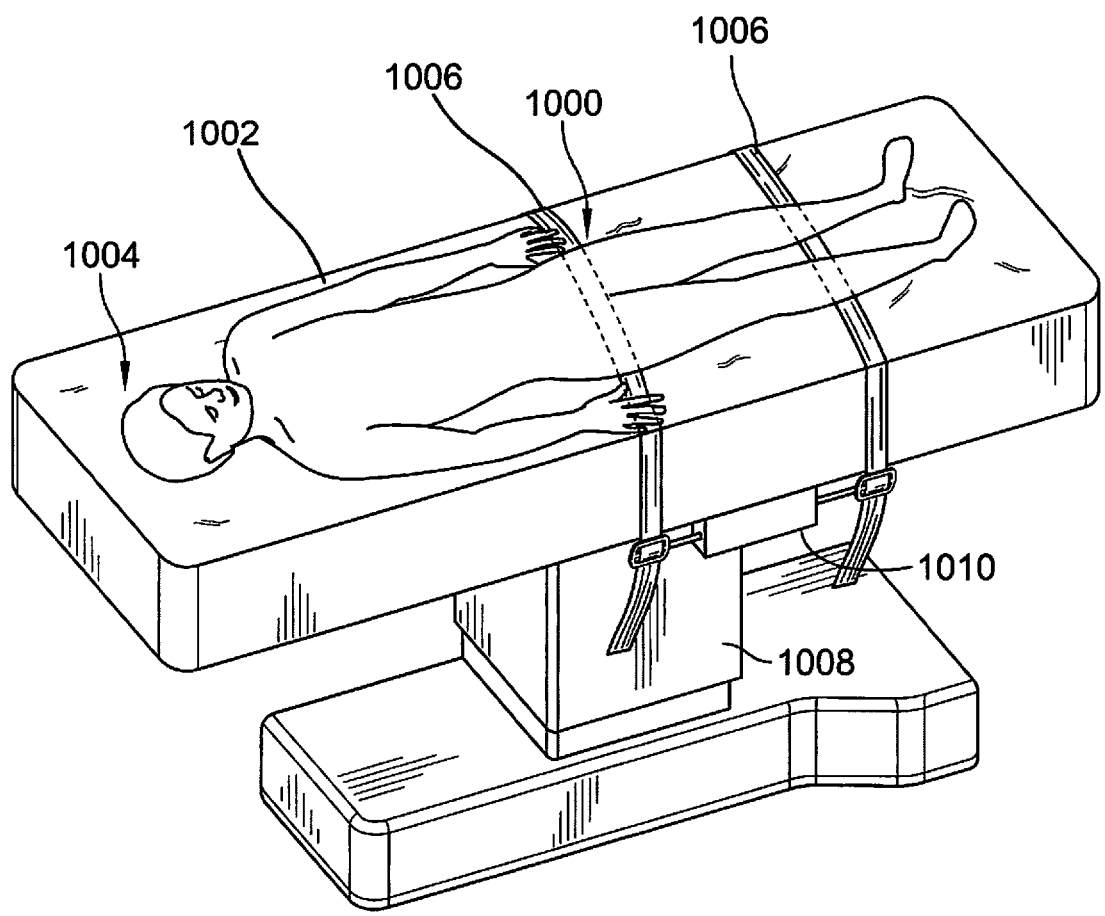
FIG. 25 is a perspective view from a head end on the patient's right of a patient support apparatus of a thermally conductive strips coupled to the patient support apparatus.

Referring now to FIG. 25, thermally conductive strips 1000 are shown. The thermally conductive strip 1000 is designed to be coupled to a sheet or ticking 1002 that encloses a patient support surface 1004. The ticking 1002 may be made of urethane, fabric, or nylon. The thermally conductive strip 1000 includes thermally conductive fibers 1006. In some embodiments, the thermally conducive fibers 1006 may be embedded into ceramic fibers and/or integrated into removable adhesive layer to allow the thermally conductive strip 1000 to be removable and repositionable on the ticking 1002.

The thermally conductive strips 1000 is configured to be positioned underneath areas of the patient's body prone to pressure ulcers when the patient is supported in a supine or prone position on the patient support surface 1004. For example, as shown in FIG. 25, the thermally conductive strips 1000 are horizontally positioned at a sacral region and a heel region. Depending on the patient, the thermally conductive strips 1000 may be removed and repositioned on the patient support surface 1004 in order to underlie the particular area of the patient's body. It should be appreciated that the thermally conductive strips may be disposable.

The thermally conductive strip 1000 is connected to a heat sink 1008 at ends 1010 of the thermally conductive fibers 1006 on at least one side of the ticking 1002 via a connector 1008. The heat sink 1008 may be a phase-change material (PCM), other cold source, or a patient support surface made of conductive metals. The heat sink 1008 is configured to withdraw and dissipate heat from the patient's body so as to provide preventative cooling to reduce the risk of breakdown at a vulnerable site on the patient's skin.

Figure 26:
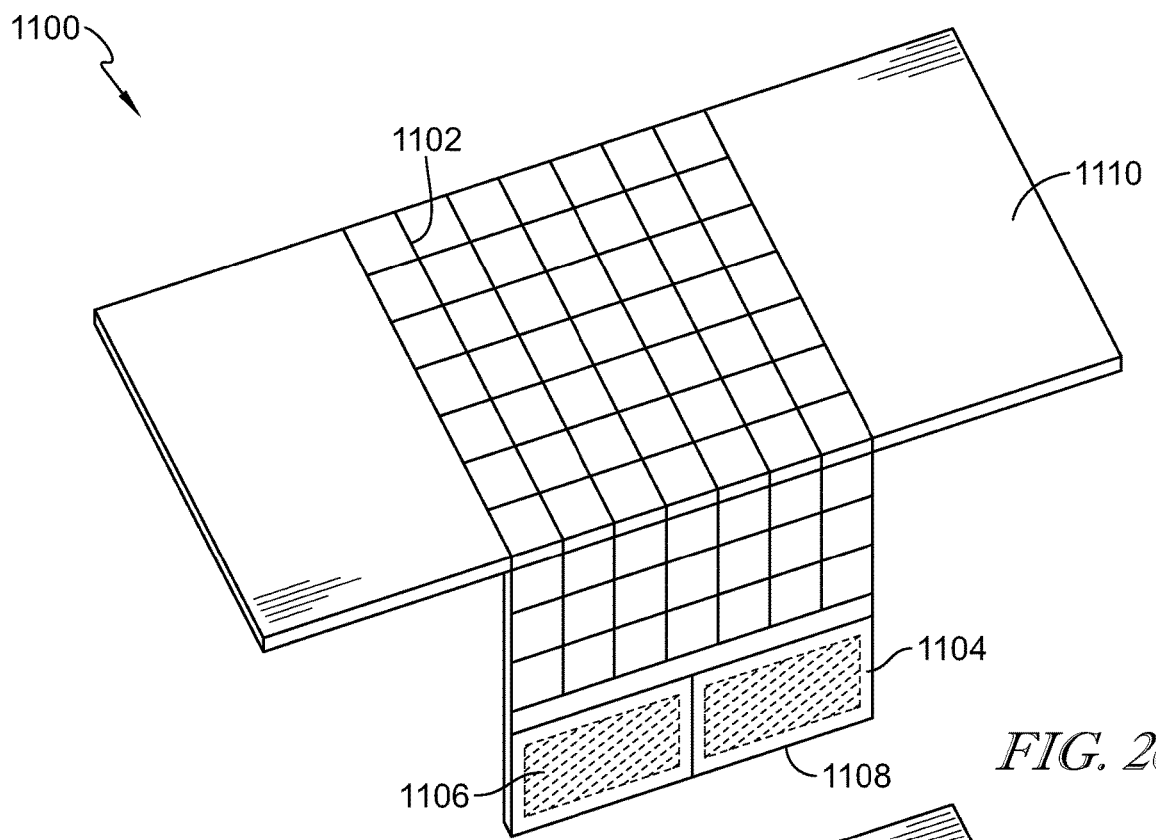
FIG. 26 is a perspective view of a first embodiment of a thermally conductive mat.
Figure 27:
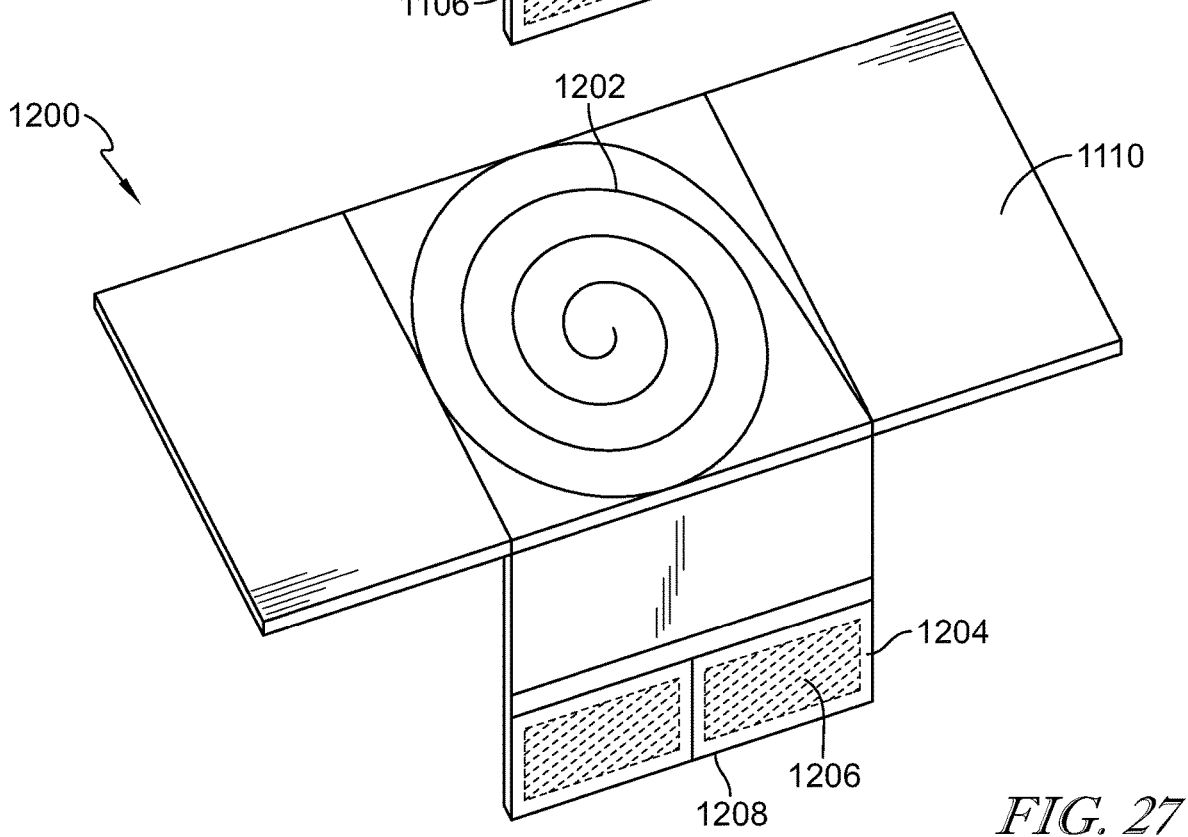
FIG. 27 is a perspective view of a second embodiment of a thermally conductive mat.

Referring now to FIGS. 26 and 27, thermally conductive mats 1100, 1200 are shown. The thermally conductive mats 1100, 1200 are designed to be positioned on a patient support surface 1110, such as a surface of a stretcher, an operating table, or a bed that supports a patient. In one embodiment, as shown in FIG. 26, the thermally conductive mat 1100 includes highly conductive carbon fibers 1102, which extends toward a compartment 1104 at an end 1108 of the thermally conductive mat 1100. The thermally conductive carbon fibers 1102 form a mesh configuration which extends into the compartment 1104. The thermally conductive mat 1100 is designed to underlie a patient's body region subject to pressure ulcers and withdraw heat from the patient's body. When the thermally conductive mat 1100 is positioned underneath the patient supported on the patient support surface 1110, the compartment 1104 is designed to rest below the patient support surface 1110. The compartment 1104 is configured to receive a removable heat sink 1106, such as a PCM cooling insert, an ice pack, or other material that will drive a chemical endothermic reaction to withdraw the heat. The heat sink 1106 is configured to withdraw and dissipate heat from the patient's body so as to provide preventative cooling to reduce the risk of breakdown at a vulnerable site on the patient's skin.

Illustratively, in use the thermally conductive mat 1100 may provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a heat sink having an appropriate size and stability temperature for the patient and the vulnerable area. In such embodiment, the removable heat sink may be replaceable without removing the entire thermally conductive mat 1100 from the patient support surface 1110. Once the removable heat sink is received in the compartment 1104, the removable heat sink maintains the cool temperature to withdraw the heat from the thermally conductive mat 1100 underneath the patient's skin. At each intersection of the mesh of thermally conductive fibers, the system may be fused to allow or disallow thermal flow as a way to control the location and amount of heat flow.

In another embodiment, as shown in FIG. 27, the thermally conductive mat 1200 includes highly conductive carbon fibers 1202, which extends toward a compartment 1204 at an end 1208 of the thermally conductive mat 1200. In this embodiment, the thermally conductive carbon fibers 1202 form a spiral configuration which extends into the compartment 1204. The spiral configured carbon fibers 1202 is designed to be concentrated at the center of the thermally conductive mat 1200 and is configured to provide a focal heat transfer from or to an area of the patient's skin positioned at the center of the thermally conductive mat 1200. The mesh and spiral illustrative examples are only to show concepts of the myriad of ways in which the thermally conductive fibers may be arranged. Other non-limiting examples include spirals under the anatomical area with conductive fibers radiating out from the spiral, a spiral under the anatomical area that overlay a mesh of conductive fibers, and the like.

The thermally conductive mat 1200, similar to the thermally conductive mat 1100, is designed to underlie a patient's body region subject to pressure ulcers and withdraw heat from the patient's body. When the thermally conductive mat 1200 is positioned underneath the patient supported on the patient support surface 1210, the compartment 1204 is designed to rest below the patient support surface 1110. The compartment 1204 is configured to receive a removable heat sink 1206, such as a PCM cooling insert, an ice pack, or other material that will drive a chemical endothermic reaction to withdraw the heat. The heat sink 1106 is configured to withdraw and dissipate heat from the patient's body so as to provide preventative cooling to reduce the risk of breakdown at a vulnerable site on the patient's skin.

Illustratively, in use the thermally conductive mat 1200 may provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a heat sink having an appropriate size and stability temperature for the patient and the vulnerable area. In such embodiment, the removable heat sink may be replaceable without removing the entire thermally conductive mat 1200 from the patient support surface 1210. Once the removable heat sink is received in the compartment 1204, the removable heat sink maintains the cool temperature to withdraw the heat from the thermally conductive mat 1200 underneath the patient's skin.

In both embodiments, portions of the thermally conductive mats 1100, 1200 that are not under the patient's body may be cooled convectively using ambient air, a closed convective loop, or a fan to efficiently and effectively remove the heat from the patient's body. The PCM cooling pack is replaceable and the thermally conductive mats 1100, 1200 may be cleaned and reused.

Although described as providing focal cooling of the vulnerable site, it should be understood that in some embodiments the thermally conductive mats 1100, 1200 may be used with one or more PCM heating inserts, that is, a PCM insert configured for a higher stability temperature, such as between 100° F. and 105° F. to provide treatment to the skin.

Figure 28:
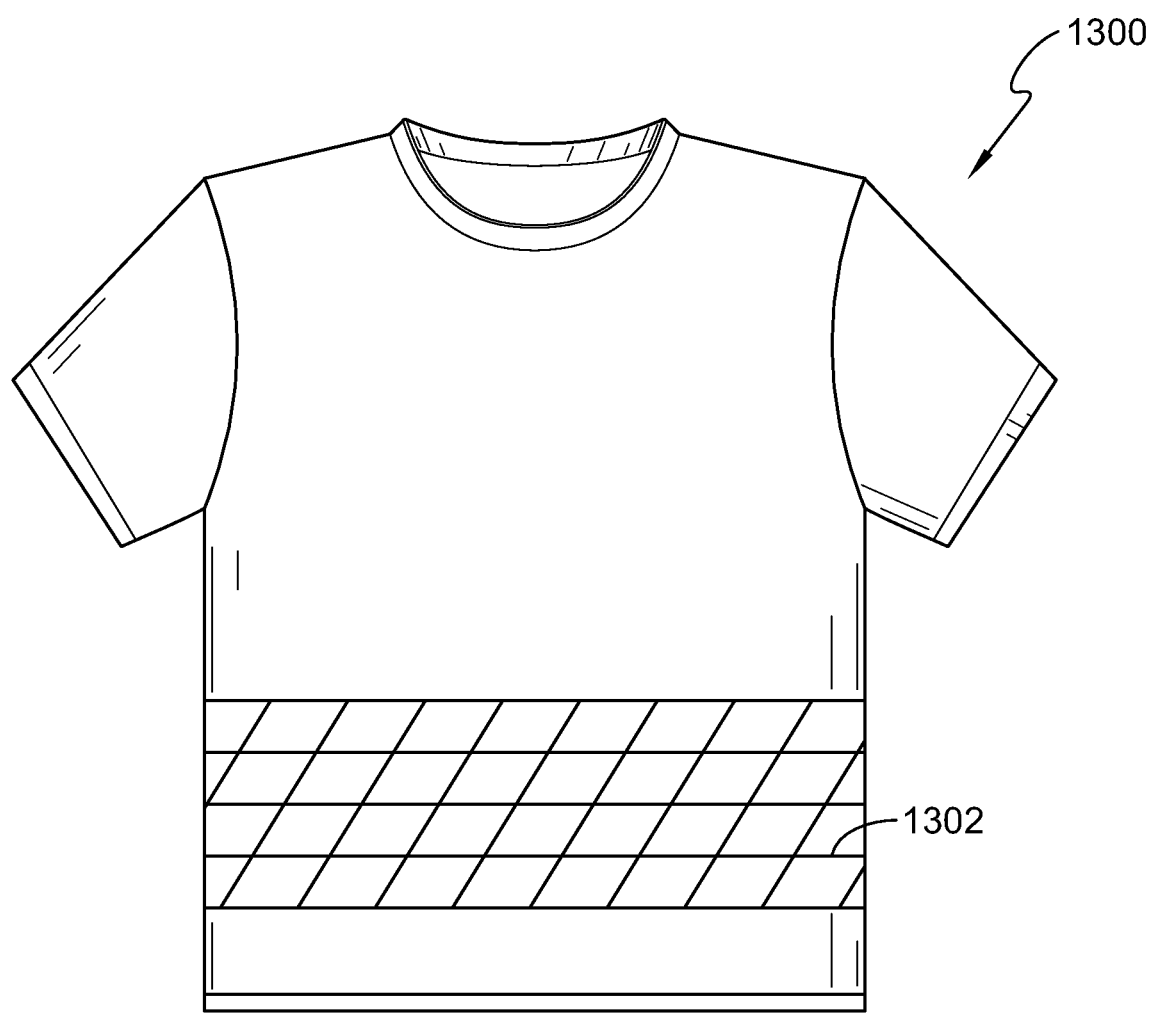
FIG. 28 is a front side view of a thermally conductive garment.

Referring now to FIG. 28, a thermally conductive garment 1300 is shown. The thermally conductive garment 1300 includes a network of thermally conductive carbon fibers 1302 in the torso region. In some embodiments, a portion of the thermally conductive garment 1300 that is exposed to ambient air may be cooled convectively using ambient air, a closed convective loop, or a fan to efficiently and effectively remove the heat from the patient's body. In some embodiments, the thermally conductive garment 1300 is used with a thermally conductive mat, similar to the thermally conductive mats 1100, 1200 shown in FIGS. 26 and 27. In such embodiment, the network of thermally conductive fibers 1302 is configured to contact the thermally conductive mat, which is in turn connected to a heat sink. It should be appreciated that the thermally conductive garment may be embodied as underwear or a blanket.

Referring now to FIGS. 29-32, a focal cooling device 1400 is shown. The focal cooling device 1400 includes a protective upper layer 1402, a middle layer 1404, and a lower adhesive layer 1406. The focal cooling device 1400 further includes a PCM insert 1408 positioned between the protective upper layer 1402 and the middle layer 1404. The lower adhesive layer 1406 is configured to attach the patient's skin subject to pressure ulcers. The focal cooling device 1400 is configured to withdraw heat from the patient's skin, particularly at a center cooling region 1416 of the focal cooling device 1400. The PCM insert 1408 includes a phase change material 1412 and thermally conductive fibers 1410. The phase change material 1412 may be in carrier medium such as an elastomer (in foam or non-foam form), a gel, or oil. In some embodiments, the conductive fibers 1410 may be pitch-based carbon fiber. It should be understood that the disclosed PCM inserts identified herein may be omitted and replaced with other types of heat sources or heat sinks.

Figure 29:
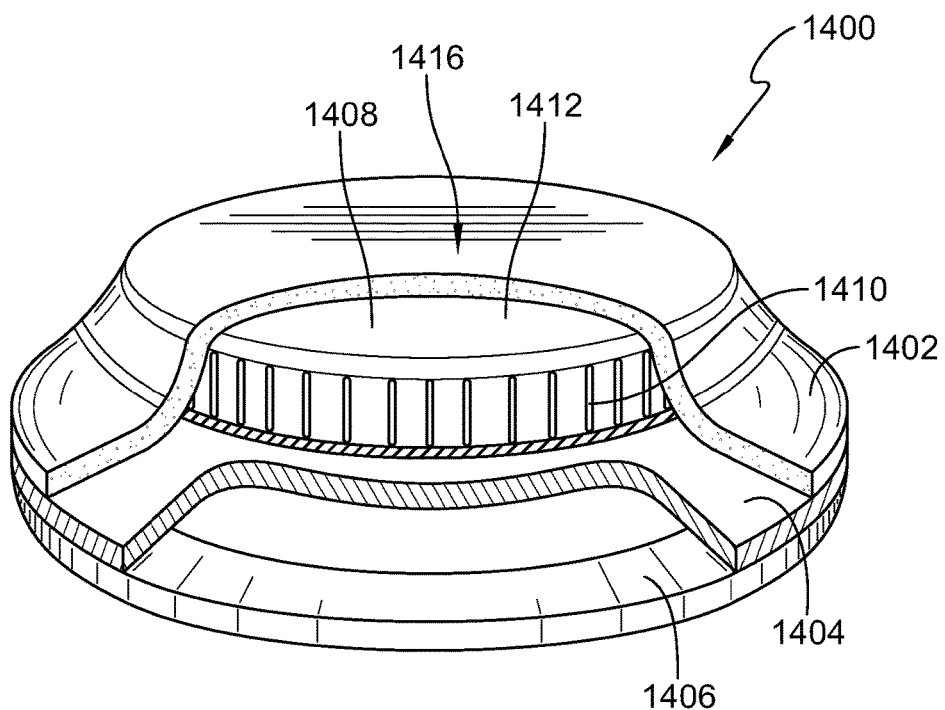
FIG. 29 is a prospective view of a focal cooling device having a first embodiment of a phase change material.
Figure 30:
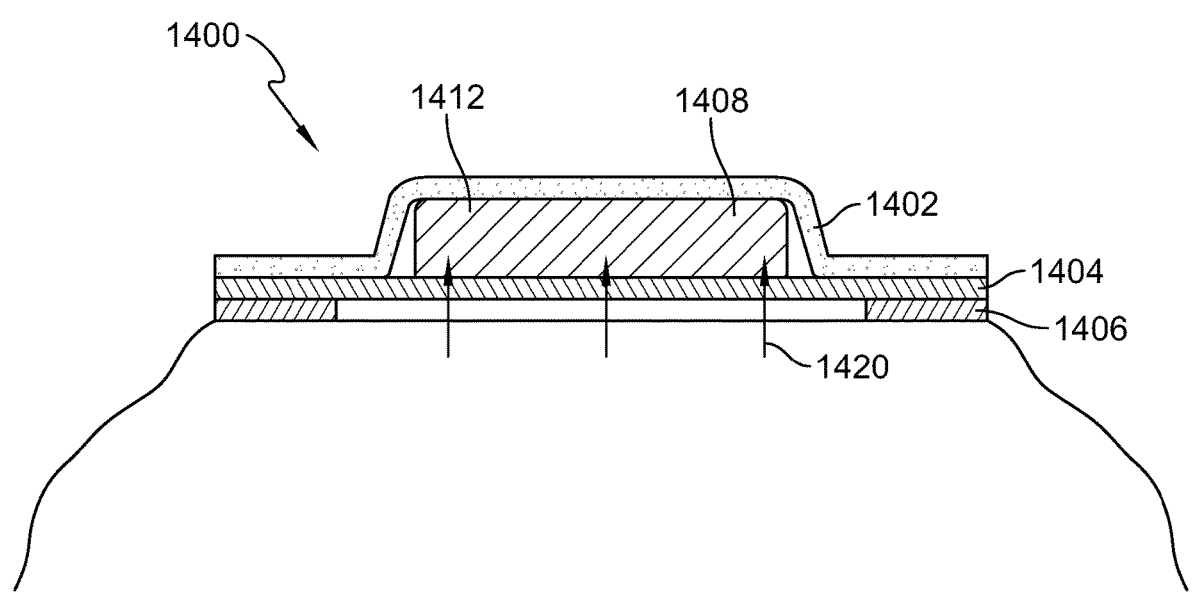
FIG. 30 is a prospective view of a second embodiment of a phase change material.

In some embodiments, as shown in FIG. 29, the conductive fibers 1410 may extend vertically along edges of the PCM insert 1408 to ensure that heat is evenly distributed throughout the depth of the PCM insert 1408. As further shown in FIG. 30, the PCM insert 1408 is configured to underlie the patient's anatomic site to withdraw heat away from that anatomic site by conducting heat along the conductive fibers 1410 upwardly toward the protective upper layer 1402 in the direction of arrows 1420.

Figure 31:
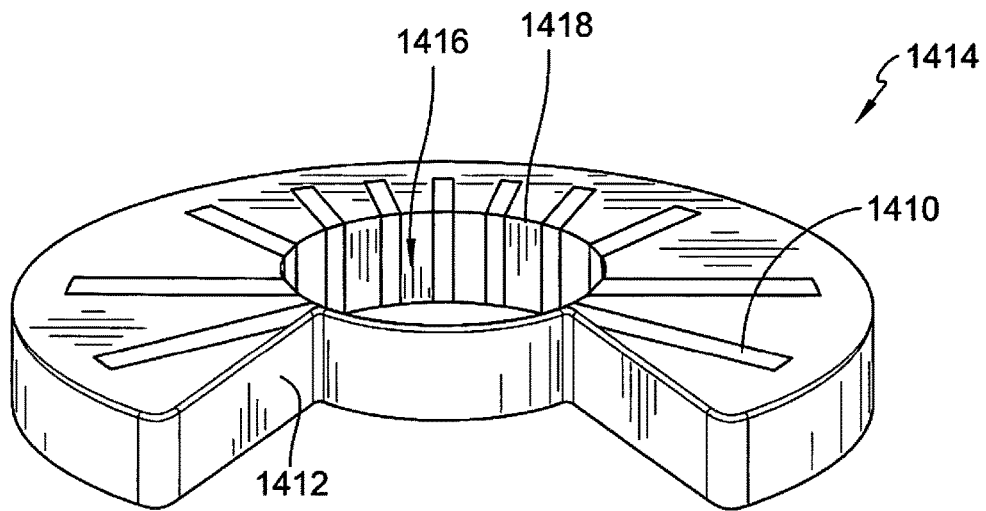
FIG. 31 is a cross-sectional side view of the focal cooling device of FIG. 29.
Figure 32:
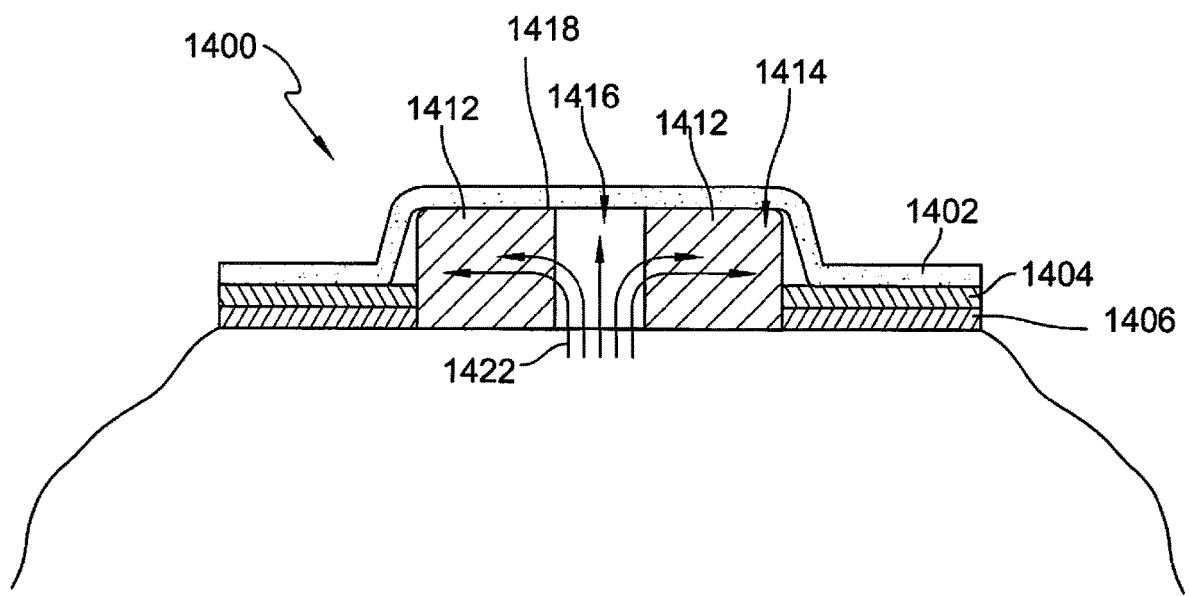
FIG. 32 is a cross-sectional side view of the focal cooling device of FIG. 30.

In some embodiments, as shown in FIG. 31, a PCM insert 1414 may include conductive fibers 1410 that extend radially to conduct heat from an open core 1418 at the center cooling region 1416 to broader areas of the PCM insert 1414, particularly in the peripheries of the focal cooling device. As further shown in FIG. 32, the open core 1418 is configured to underlie the patient's anatomic site to withdraw heat away from that anatomic site by conducting heat along the conductive fibers 1410 to the peripheries of the PCM insert 1414 in the direction of arrows 1422.

In some embodiments, the focal cooling device 1400 is designed to be active during a surgical procedure. In such embodiment, the PCM insert 1408 is not removable or replaceable, and the focal cooling device 1400 may be disposable after the surgical procedure. However, it should be appreciated that, in some embodiments, the focal cooling device 1400 may include an opening in order to remove and replace the PCM insert.

Illustratively, in use the focal cooling device 1400 may provide preventative cooling to reduce the risk of breakdown at a vulnerable site on the patient's skin. A healthcare provider may determine a temperature for focal cooling of the vulnerable site, such as the patient's sacral area. The cooling temperature may be selected to cool the skin as much as possible without causing vasoconstriction for the particular patient at the particular vulnerable site. The healthcare provider may select a focal cooling device 1400 having a PCM insert 1408 with an appropriate size and stability temperature for the patient and the vulnerable area. Once the selected cooling device 1400 is placed on the patient's skin, the PCM insert 1408 maintains the cool temperature to withdraw the heat from the patient's skin at a center cooling region of the focal cooling device 1400.

Although described as providing focal cooling of the vulnerable site, it should be understood that in some embodiments the focal device may be used with one or more PCM heating inserts, that is, a PCM insert configured for a higher stability temperature, such as between 100° F. and 105° F. to provide treatment to the skin.

The various configurations of the embodiments shown in FIGS. 1-32 have several common advantages. The embodiments provide focal cooling to vulnerable areas to help prevent inflammation and tissue breakdown. Particularly, the embodiments may prevent Stage III/IV pressure ulcers and/or deep tissue injury, which may represent a significant cost of wound treatment. The embodiments are compatible with many care settings (e.g., operating room, emergency department, and/or imaging settings) and may not be susceptible to interference from patient linens. Additionally, the embodiments may provide passive skin temperature control without the need for complicated and/or expensive micro climate management (MCM) equipment or other control systems. Furthermore, the embodiments may provide flexible patient care options and reduced cost through the use of interchangeable and reusable phase-change material cooling inserts.

Although certain illustrative embodiments have been described in detail above, variations and modifications exist within the scope and spirit of this disclosure as described and as defined in the following claims.

The invention claimed is:

1. An apparatus for modifying the temperature of a person's skin in a localized region, the apparatus comprising:
   a skin contacting surface;
   a heat sink having a first temperature different from the temperature of the skin being contacted by the skin contacting surface to create a temperature gradient between the skin and the heat sink; and
   a flow path configured to allow heat to flow between the skin and the heat sink,
   wherein the apparatus comprises:
   a thermoelectric module that includes a first surface that is configured to be the skin contacting surface and a non-adhesive surface, and a second surface, positioned away from the skin contacting surface;
   an adhesive layer configured to overlie the thermoelectric module, on the second surface, to secure the thermoelectric module to the skin; and
   a power source operable to cause the thermoelectric module to transfer heat between the first surface of the thermoelectric module and the second surface of the thermoelectric module;
   wherein the flow path is thermally conductive and facilitates the transfer of heat between the heat sink and the second surface of thermoelectric module.

2. The apparatus of claim 1, wherein the apparatus further comprises a temperature sensor for determining the temperature of the surface of the skin.

3. The apparatus of claim 2, wherein the apparatus further comprises a pressure sensor for determining the pressure applied to the surface of the skin.

4. The apparatus of claim 3, wherein the apparatus further comprises a moisture sensor for determining the moisture at the surface of the skin.

5. The apparatus of claim 1, wherein the apparatus further comprises a blood perfusion sensor for determining the perfusion rate.

6. The apparatus of claim 5, wherein the power source is configured to vary the operation of the thermoelectric module in response to a condition at the surface of the skin detected by one or more sensors.

7. The apparatus of claim 6, wherein the power source wirelessly transfers power to the thermoelectric module.

8. The apparatus of claim 1, wherein the heat sink comprises a phase-change material.

9. An apparatus for modifying the temperature of a person's skin in a localized region, the apparatus comprising:
a thermoelectric module that includes a first surface that is configured to be the skin contacting surface and a non-adhesive surface, and a second surface, positioned away from the skin contacting surface;
an adhesive layer configured to overlie the thermoelectric module, on the second surface, to secure the thermoelectric module to the skin;
a power source operable to cause the thermoelectric module to transfer heat between the first surface of the thermoelectric module and the second surface of the thermoelectric module;
at least one sensor for detecting a condition of the skin;
wherein a heat transfer flow path facilitates the transfer of heat between the heat sink and the second surface of thermoelectric module, and
wherein the power source is configured to vary the operation of the thermoelectric module in response to a condition at the surface of the skin detected by the at least one sensor.

10. The apparatus of claim 9, wherein the sensor comprises a temperature sensor for determining the temperature of the surface of the skin.

11. The apparatus of claim 9, wherein the sensor comprises a pressure sensor for determining the pressure applied to the surface of the skin.

12. The apparatus of claim 9, wherein the sensor comprises a moisture sensor for determining the moisture at the surface of the skin.

13. The apparatus of claim 9, wherein the sensor comprises a blood perfusion sensor for determining the perfusion rate.

14. The apparatus of claim 9, wherein the power source wirelessly transfers power to the thermoelectric device.

15. The apparatus of claim 9, wherein at least one sensor comprises a temperature sensor for determining the temperature of the surface of the skin and at least one sensor comprises a moisture sensor for determining the moisture at the surface of the skin.

* * * * *